US006424866B2

(12) United States Patent
Mika et al.

(10) Patent No.: US 6,424,866 B2
(45) Date of Patent: *Jul. 23, 2002

(54) APPARATUS AND METHOD FOR TIMING THE DELIVERY OF NON-EXCITATORY ETC SIGNALS TO A HEART

(75) Inventors: Yuval Mika, Zichron-Yaacov (IL); David Prutchi, Lake Jackson, TX (US); Ziv Belsky; Yoav Kimchy, both of Haifa (IL)

(73) Assignee: Impulse Dynamics N.V., Curacao (AN)

( * ) Notice: Subject to any disclaimer, the term of this patent is extended or adjusted under 35 U.S.C. 154(b) by 0 days.

This patent is subject to a terminal disclaimer.

(21) Appl. No.: 09/841,891

(22) Filed: Apr. 25, 2001

Related U.S. Application Data

(63) Continuation of application No. 09/276,460, filed on Mar. 25, 1999, now Pat. No. 6,263,242.

(51) Int. Cl.[7] .................................................. A61N 1/36
(52) U.S. Cl. ............................................. 607/9; 607/25
(58) Field of Search ............................... 607/9, 11, 25, 607/68; 600/510

(56) References Cited

U.S. PATENT DOCUMENTS

| 4,506,680 A | 3/1985 | Stokes |
| 4,554,922 A | 11/1985 | Prystowsky et al. |
| 4,559,947 A | 12/1985 | Renger et al. |

(List continued on next page.)

FOREIGN PATENT DOCUMENTS

| WO | WO 97/25098 | 7/1997 |
| WO | WO 98/10828 | 3/1998 |
| WO | WO 98/10829 | 3/1998 |

(List continued on next page.)

OTHER PUBLICATIONS

"A Model Analysis of Aftereffects of High–Intensity DC Stimulation on Action Potential of Ventricular Muscle" published by Sakuma et al., in IEEE Transactions on Biomedical Engineering, 45(2) pp. 258–267, 1998.

(List continued on next page.)

Primary Examiner—Jeffrey R. Jastrzab
(74) Attorney, Agent, or Firm—Reed Smith LLP; William H. Dippert

(57) ABSTRACT

A method and devices for timing the delivery of non-excitatory signals for modifying myocardial contractility of a portion of the heart are disclosed. The method includes the steps of applying electrodes to a plurality of cardiac sites, sensing electrical activity in a first cardiac site through a first electrode for detecting a first electrical depolarization event within a beat cycle, sensing electrical activity in a second cardiac site through a second electrode for detecting a second electrical depolarization event within the beat cycle, and applying a non-excitatory signal to the heart at or near at least the second cardiac site through at least one of the electrodes in response to detecting the second electrical depolarization event within an alert window period. The alert window period starts at a first delay from the time of detection of the first electrical depolarization event and has a first duration. The applying of the non-excitatory signal is delayed from the time of detecting of the second electrical depolarization event. The method may include steps for reducing the probability of delivering of improperly timed non-excitatory signals due to electrical noise and/or ectopic beats and may also include steps for preventing delivery of multiple non-excitatory signals at or near the second cardiac site within a single cardiac beat cycle. Preferably, the first cardiac site is located about the right ventricle or the right atrium of the heart and the second cardiac site is located about the left ventricle of the heart. The devices may also be adapted for pacing the heart and/or for delivering defibrilation signals to the heart.

32 Claims, 7 Drawing Sheets

U.S. PATENT DOCUMENTS

| | | |
|---|---|---|
| 4,566,456 A | 1/1986 | Koning et al. |
| 4,651,716 A | 3/1987 | Forester et al. |
| 4,679,572 A | 7/1987 | Baker, Jr. |
| 4,690,155 A | 9/1987 | Hess |
| 4,830,006 A | 5/1989 | Haluska et al. |
| 4,971,058 A | 11/1990 | Pless et al. |
| 5,003,976 A | 4/1991 | Alt |
| 5,022,396 A | 6/1991 | Watanabe |
| 5,083,564 A | 1/1992 | Scherlag |
| 5,129,394 A | 7/1992 | Mehra |
| 5,154,501 A | 10/1992 | Svenson et al. |
| 5,156,149 A | 10/1992 | Hudrlik |
| 5,161,527 A | 11/1992 | Nappholz et al. |
| 5,172,699 A | 12/1992 | Svenson et al. |
| 5,184,620 A | 2/1993 | Cudahy et al. |
| 5,205,284 A | 4/1993 | Freeman |
| 5,281,219 A | 1/1994 | Kallock |
| 5,305,745 A | 4/1994 | Zacouto |
| 5,353,800 A | 10/1994 | Pohndorf |
| 5,368,040 A | 11/1994 | Carney |
| 5,391,192 A | 2/1995 | Lu et al. |
| 5,398,683 A | 3/1995 | Edwards et al. |
| 5,425,363 A | 6/1995 | Wang |
| 5,443,485 A | 8/1995 | Housworth et al. |
| 5,443,489 A | 8/1995 | Ben-Haim |
| 5,447,520 A | 9/1995 | Spano et al. |
| 5,476,484 A | 12/1995 | Hedberg |
| 5,482,052 A | 1/1996 | Lerner |
| 5,531,764 A | 7/1996 | Adams et al. |
| 5,549,646 A | 8/1996 | Katz et al. |
| 5,556,421 A | 9/1996 | Prutchi et al. |
| 5,587,200 A | 12/1996 | Lorentz et al. |
| 5,601,609 A | 2/1997 | Duncan |
| 5,683,431 A | 11/1997 | Wang |
| 5,749,906 A | 5/1998 | Kieval et al. |
| 5,755,740 A | 5/1998 | Nappholz |
| 5,782,876 A | 7/1998 | Flammang |
| 5,782,881 A | 7/1998 | Lu et al. |
| 5,800,464 A | 9/1998 | Kieval |
| 5,814,079 A | 9/1998 | Kieval |
| 5,871,506 A | 2/1999 | Mower |
| 6,233,072 B1 | 4/2001 | Mika et al. |
| 6,233,487 B1 | 5/2001 | Mika et al. |

FOREIGN PATENT DOCUMENTS

| | | |
|---|---|---|
| WO | WO 98/10830 | 3/1998 |
| WO | WO 98/10831 | 3/1998 |
| WO | WO 98/10832 | 3/1998 |
| WO | WO 99/03533 | 1/1999 |
| WO | WO 00/42914 | 7/2000 |
| WO | WO 00/57947 | 10/2000 |
| WO | WO 00/57952 | 10/2000 |
| WO | WO 00/74552 | 12/2000 |
| WO | WO 01/00137 | 1/2001 |
| WO | WO 01/13992 | 3/2001 |
| WO | WO 00/27475 | 5/2001 |
| WO | WO 01/30139 | 5/2001 |
| WO | WO 01/30436 | 5/2001 |
| WO | WO 01/30445 | 5/2001 |

OTHER PUBLICATIONS

Horner et al. titled "Electrode for Recording Direction of Activation, Conduction Velocity and Monophasic Action Potential of Myocardium", published in American Journal of Physiology, vol. 272 (Heart Circ. Physiol. 41), pp. H1917–H1927, 1997.

Koller, et al., titled "Relation Between Repolarization and Refractoriness During Programmed Electrical Stimulation in the Human Right Ventricle", published in Circulation, 91(9), 2378–2384, 1995.

"Neural–Network–Based Adaptive Matched Filtering for QRS Detection" by Qiuzhen Xue et al., IEEE Transactions on Biomedical Engineering, vol. 39, No. 4, Apr. 1992.

"Identification of Ventricular Tachycardia with Use of the Morphology of the Endocardial Electrogram" by Jonathan J. Langberg. et al. Circulation vol. 77. No. 6, Jun. 1988.

P. Fu and B.J. Bardakjian, titled "System Identification of Electrically Coupled Smooth Muscle Cells: The Passive Electrical Properties", published in IEEE Transactions on Biomedical Engineering, 38(11), pp. 1130–1140, 1991.

H. Antoni, et al. "Polarization Effects of Sinusoidal 50–Cycle Alternating Current on Membranr Potential of Mammalian Cardiac Fibres", Pflugers Arch. 314, pp. 274–291 (1970).

"Classification of Cardiac Arrhythmias Using Fuzzy Artmap" by Fredric M. Ham and Soowhan Han; IEEE Transactions on Biomedical Engineeering, vol. 43, No. 4, Apr. 1996.

APPARATUS AND METHOD FOR TIMING THE DELIVERY OF NON-EXCITATORY ETC SIGNALS TO A HEART

RELATED U.S. APPLICATIONS

This application is a continuation of U.S. patent application Ser. No. 09/276,460, to Mika et al., entitled "APPARATUS AND METHOD FOR TIMING THE DELIVERY OF NON-EXCITATORY ETC SIGNALS TO A HEART", filed Mar. 25, 1999, now U.S. Pat. No. 6,263,242, incorporated herein by reference in it's entirety.

FIELD OF THE INVENTION

The present invention relates generally to the field of methods and medical devices for modulating cardiac muscle activity and contractility and for cardiac pacing and more specifically to the field of methods for determining timing of delivery of non-excitatory excitable tissue control (ETC) signals to the heart.

BACKGROUND OF THE INVENTION

Excitable tissue control (ETC) devices are devices which modulate the activity of excitable tissues by application of non-excitatory electrical field signals to the excitable tissue through suitable electrodes in contact with the tissue. For example, ETC devices may be used, inter alia, to increase or decrease the contractility of cardiac muscle in vitro, in vivo and in situ., as disclosed in detail in PCT application PCT/IL97/00012 (International Publication Number WO 97/25098) to Ben-Haim et al., titled "ELECTRICAL MUSCLE CONTROLLER", incorporated herein by reference. Other methods and applications of ETC devices are disclosed in PCT application PCT/IL97/00231 (International Publication Number WO 98/10828) titled "APPARATUS AND METHOD FOR CONTROLLING THE CONTRACTILITY OF MUSCLES" to Ben Haim et al., incorporated herein by reference, PCT application PCT/IL97/00232 (International Publication Number WO 98/10829) titled "DRUG-DEVICE COMBINATION FOR CONTROLLING THE CONTRACTILITY OF MUSCLES" to Ben Haim et al., incorporated herein by reference and PCT application PCT/IL97/00233 (International Publication Number WO 98/10830) titled "FENCING OF CARDIAC MUSCLES" to Ben Haim et al., incorporated herein by reference, PCT application PCT/IL97/00235 (International Publications Number WO 98/10831) to Ben Haim et al., titled "CARDIAC OUTPUT CONTROLLER", incorporated herein by reference.

Further applications of the ETC including devices combining cardiac pacing and cardiac contractility modulation are disclosed in PCT Application, International Publication No. WO 98/10832, titled "CARDIAC OUTPUT ENHANCED PACEMAKER" to Ben Haim et al., co-assigned to the assignee of the present application. Such ETC devices function by applying to selected cardiac segments non-excitatory electrical signals of suitable amplitude and waveform, appropriately timed with respect to the heart's intrinsic electrical activity or with respect to paced cardiac electrical activity. The contraction of the selected segments can be modulated to increase or decrease the stroke volume of the heart. The timing of the ETC signals must be carefully controlled since application of the ETC signal to the myocardium at inappropriate times may be arrhythmogenic. The ETC signal must therefore be applied to the selected cardiac segment within a defined time interval during which the selected cardiac segment will not be stimulated by the ETC signal.

As disclosed in International Publication No. WO 98/10832, the ETC signal may be timed relative to a trigger signal which is also used as a pacing trigger, or may be timed relative to locally sensed depolarizing electrogram signals.

Timing of the delivery of ETC signals relative to the time of detection of locally sensed electrogram signals may present certain practical problems. For example, triggering of the ETC signal by any locally detected depolarizing signals irrespective of the time of detection of the depolarizing signal within the cardiac beat cycle, may increase the probability of spurious detection of noise signals or of ectopic beats such as premature ventricular contractions (PVCs) or the like, which may lead to delivery of improperly timed and potentially arrhythmogenic ETC signals. It is therefore desirable to have a method for determining proper timing of the delivery of ETC signals without unduly increasing the probability of delivering an improperly timed ETC signal caused by spurious noise detection or by detection of ectopic beats.

SUMMARY OF THE INVENTION

There is therefore provided, in accordance with a preferred embodiment of the present invention, a method for timing the delivery of a non-excitatory signal to a heart within a cardiac beat cycle. The method includes the steps of applying electrodes to a plurality of cardiac sites, sensing electrical activity in at least a first site of the plurality of cardiac sites through at least a first electrode of the electrodes for detecting a first electrical depolarization event within the beat cycle, sensing electrical activity in at least a second site of the plurality of sites through at least a second electrode of the electrodes for detecting at least a second electrical depolarization event within the beat cycle, and applying the non-excitatory signal to at least one of the cardiac sites through at least one of the electrodes in response to detecting the second electrical depolarization event within an alert window period. The alert window period starts at a first delay from the time of detection of the first electrical depolarization event and has a first duration. The applying is delayed from the time of detecting of the second electrical depolarization event.

Furthermore, in accordance with another preferred embodiment of the present invention, the method includes the step of inhibiting the applying of the cardiac non-excitatory signal of the step of applying in response to detecting at the second site a third electrical depolarization event preceding the second electrical depolarization event. The third electrical depolarization event is detected within an inhibition window period. The inhibition window period starts at a second delay from the time of detection of the first electrical depolarization event and terminates before or at the time of starting of the alert window period. The second delay is smaller than the first delay.

Furthermore, in accordance with another preferred embodiment of the present invention, the step of inhibiting includes the step of initiating an inhibition refractory period. The inhibition refractory period starts at the time of detecting of the third electrical depolarization event and has a second duration. The sensing of the electrical activity in the second site is disabled during the inhibition refractory period.

Furthermore, in accordance with another preferred embodiment of the present invention, the sensing of the second step of sensing at the second site starts after the end of a refractory time period. The refractory period begins at the time of detection of the first electrical depolarization event and has a refractory period duration.

Furthermore, in accordance with another preferred embodiment of the present invention, the method further includes the step of pacing the heart by applying at least one pacing pulse to the heart through the first electrode. The refractory period prevents the sensing of electrical artifact signals by the second electrode due to the pacing pulse.

Furthermore, in accordance with another preferred embodiment of the present invention, the first site is located in or about the right ventricle of the heart and the second site is located in or about the left ventricle of the heart.

Furthermore, in accordance with another preferred embodiment of the present invention, the first site is located in or about the right atrium of the heart and the second site is located in or about the left ventricle of the heart.

Furthermore, in accordance with another preferred embodiment of the present invention, the method further includes the step of pacing the heart by applying within the beat cycle a pacing pulse to at least one of the electrodes prior to second step of applying.

Furthermore, in accordance with another preferred embodiment of the present invention, the first site is located in or about the right ventricle of the heart and the at least second site is located in or about the left ventricle of the heart.

Furthermore, in accordance with another preferred embodiment of the present invention, the step of pacing includes pacing the right ventricle by applying a pacing pulse to the first electrode or to one of the electrodes applied to the right ventricle.

Furthermore, in accordance with another preferred embodiment of the present invention, the step of pacing includes pacing the left ventricle by applying a pacing pulse to the second electrode or to one of the electrodes applied to the left ventricle.

Furthermore, in accordance with another preferred embodiment of the present invention, the step of pacing includes pacing the right atrium of the heart by delivering a pacing pulse to the right atrium through one of the electrodes applied to the right atrium.

Furthermore, in accordance with another preferred embodiment of the present invention, the first site is located in or about the right atrium of the heart and the second site is located in or about the left ventricle of the heart.

Furthermore, in accordance with another preferred embodiment of the present invention, the step of pacing includes pacing the right atrium by applying a pacing pulse to the first electrode or to one of the electrodes applied to the right atrium.

Furthermore, in accordance with another preferred embodiment of the present invention, the step of pacing includes pacing the left ventricle by applying a pacing pulse to the second electrode or to one of the electrodes applied to the left ventricles.

Furthermore, in accordance with another preferred embodiment of the present invention, the step of pacing includes pacing the right ventricle of the heart by delivering a pacing pulse to the right ventricle through one of the electrodes applied to the right ventricle.

Furthermore, in accordance with another preferred embodiment of the present invention, the detecting of at least one of the first step of sensing and the second step of sensing includes detecting a depolarization event using an event detection method selected from a threshold crossing detection method, a detection method based on one or more morphological parameters of the electrical activity, a slope based detection method and any combination thereof.

Furthermore, in accordance with another preferred embodiment of the present invention, the first electrical depolarization event is an electrical depolarization wave initiated by the intrinsic pacing activity of the heart or by a pacing pulse delivered to the heart through one of the electrodes.

Furthermore, in accordance with another preferred embodiment of the present invention, the second electrical depolarization event is an electrical depolarization wave initiated by the intrinsic pacing activity of the heart or by a pacing pulse delivered to the heart through one of the electrodes.

Furthermore, in accordance with another preferred embodiment of the present invention, the applying of the non-excitatory signal of the second step of applying is performed through the second electrode.

Furthermore, in accordance with another preferred embodiment of the present invention, the applying of the step of applying is performed in response to the earliest occurring electrical depolarization event of the at least second electrical depolarization event detected within the alert window period.

Furthermore, in accordance with another preferred embodiment of the present invention, the method further including the step of initiating an alert refractory period in response to the detection of the earliest occurring electrical depolarization event. The alert refractory period starts at the time of detection of the earliest occurring electrical depolarization event and has a third duration. The alert refractory period ends within the duration of the beat cycle. During the alert refractory period, the sensing and the detecting of the second step of detecting at the second site are disabled.

Furthermore, in accordance with another preferred embodiment of the present invention, the third duration of the alert refractory period is a preset value.

Furthermore, in accordance with another preferred embodiment of the present invention, the third duration of the alert refractory period is larger than the sum of the first duration, the second delay and the maximal allowable duration of the non-excitatory signal.

There is further provided, in accordance with another preferred embodiment of the present invention, a method for timing the delivery of a non-excitatory signal to a heart within a cardiac beat cycle. The method includes the steps of sensing electrical activity in at least a first site of the heart through at least a first electrode applied to the first site for detecting a first electrical depolarization event within the beat cycle, sensing electrical activity in at least a second site of the heart through at least a second electrode applied to the second site for detecting at least a second electrical depolarization event within the beat cycle, and applying the non-excitatory signal at or in the vicinity of the second site of the heart in response to detecting the second electrical depolarization event within an alert window period. The alert window period starts at a first delay from the time of detection of the first electrical depolarization event and has a first duration. The applying is delayed from the time of detecting of the second electrical depolarization event.

Furthermore, in accordance with another preferred embodiment of the present invention, the method further includes the step of inhibiting the applying of the non-excitatory signal of the step of applying in response to detecting at the second site a third electrical depolarization event preceding the second electrical depolarization event. The third electrical depolarization event is detected within an inhibition window period. The inhibition window period starts at a second delay from the time of detection of the first electrical depolarization event, and terminates at or before the time of starting of the alert window period. The second delay is smaller than the first delay.

Furthermore, in accordance with another preferred embodiment of the present invention, the step of inhibiting includes the step of initiating an inhibition refractory period. The inhibition refractory period starts at the time of detecting of the third electrical depolarization event and has a second duration. The sensing of the electrical activity in the second site is disabled during the inhibition refractory period.

Furthermore, in accordance with another preferred embodiment of the present invention, the second duration of the inhibition refractory period is a preset duration.

Furthermore, in accordance with another preferred embodiment of the present invention, the second duration of the inhibition refractory period is equal to or larger than the value obtained by summing the inhibition window period, the first duration, the second delay and the maximal allowable duration of the non-excitatory signal.

Furthermore, in accordance with another preferred embodiment of the present invention, the step of initiating includes the step of determining the value of the second duration for the beat cycle from the time of detecting of the third electrical depolarization event within the beat cycle and from the preset values of the first duration of the alert window, the first delay and the maximal allowable duration of the non-excitatory signal.

Furthermore, in accordance with another preferred embodiment of the present invention, the second duration is larger than the value obtained by subtracting the time of detecting of the third electrical depolarization event from the sum of the first delay, the first duration, the second delay and the maximal allowable duration of the non-excitatory signal.

Furthermore, in accordance with another preferred embodiment of the present invention, the first site is located in or about the right ventricle of the heart and the second site is located in or about the left ventricle of the heart.

Furthermore, in accordance with another preferred embodiment of the present invention, the first site is located in or about the right atrium of the heart and the second site is located in or about the left ventricle of the heart.

Furthermore, in accordance with another preferred embodiment of the present invention, the method further includes the step of pacing the heart within the beat cycle by delivering a pacing pulse to the heart prior to the step of applying.

Furthermore, in accordance with another preferred embodiment of the present invention, the delivering of the pacing pulse includes applying the pacing pulse to an electrode selected from the first electrode, the second electrode and a third electrode applied to a third site of the heart.

Furthermore, in accordance with another preferred embodiment of the present invention, the first site is located in or about the right ventricle of the heart and the second site is located in or about the left ventricle of the heart.

Furthermore, in accordance with another preferred embodiment of the present invention, the step of pacing includes pacing the right ventricle by applying a pacing pulse to the first electrode or to a pacing electrode applied to the right ventricle.

Furthermore, in accordance with another preferred embodiment of the present invention, the step of pacing includes pacing the left ventricle by applying a pacing pulse to the second electrode or to a pacing electrode applied to the left ventricle.

Furthermore, in accordance with another preferred embodiment of the present invention, the step of pacing includes pacing the right atrium of the heart by delivering a pacing pulse to the right atrium through a third electrode applied to the right atrium.

Furthermore, in accordance with another preferred embodiment of the present invention, the first site is located in or about the right atrium of the heart and the second site is located in or about the left ventricle of the heart.

Furthermore, in accordance with another preferred embodiment of the present invention, the first electrode is applied to the right atrium of the heart, the second electrode is applied to the left ventricle of the heart and the third electrode is applied to the right atrium of the heart.

Furthermore, in accordance with another preferred embodiment of the present invention, the first electrode is applied the right atrium of the heart, the second electrode is applied to the left ventricle of the heart and the third site is the right ventricle of the heart.

Furthermore, in accordance with another preferred embodiment of the present invention, the method further includes the step of pacing the heart by delivering a pacing pulse to the heart prior to said step of applying through at least one electrode selected from the first electrode, the second electrode and a third electrode applied to a third site of the heart.

Furthermore, in accordance with another preferred embodiment of the present invention, the first site is located in or about the right ventricle of the heart, the second site is located in or about the left ventricle of the heart and the third site is the right atrium of the heart.

Furthermore, in accordance with another preferred embodiment of the present invention, the detecting of at least one of the first step of sensing and the second step of sensing includes detecting a depolarization event using an event detection method selected from a threshold crossing detection method, a detection method based on one or more morphological parameters of the electrical activity, a slope based detection method, and any combination thereof.

Furthermore, in accordance with another preferred embodiment of the present invention, the first electrical depolarization event is an electrical depolarization wave initiated by the intrinsic pacing activity of the heart or by a pacing pulse delivered to the heart.

Furthermore, in accordance with another preferred embodiment of the present invention, the second electrical depolarization event is an electrical depolarization wave initiated by the intrinsic pacing activity of the heart or by a pacing pulse.

Furthermore, in accordance with another preferred embodiment of the present invention, the applying of the non-excitatory signal of the step of applying is performed through the second electrode of the second step of sensing.

Furthermore, in accordance with another preferred embodiment of the present invention, the applying of the step of applying is performed in response to the detection of the earliest of the at least second electrical depolarization event detected within the alert window period.

Furthermore, in accordance with another preferred embodiment of the present invention, the method further includes the step of initiating an alert refractory period in response to the detection of the earliest occurring electrical depolarization event within the alert window period. The alert refractory period starts at the time of detection of the earliest occurring electrical depolarization event and has a third duration. The alert refractory period ends within the duration of the beat cycle. During the alert refractory period the sensing and the detecting of the second step of detecting at the second site are disabled.

Furthermore, in accordance with another preferred embodiment of the present invention, the third duration of the alert refractory period is a preset value.

Furthermore, in accordance with another preferred embodiment of the present invention, the third duration of the alert refractory period is larger than the sum of the first duration, the second delay and the maximal allowable duration of the non-excitatory signal.

There is further provided, in accordance with another preferred embodiment of the present invention, apparatus for timing the delivery of a non-excitatory signal to the heart within a cardiac beat cycle of the heart. The apparatus includes a plurality of electrodes adapted to be implanted in the heart. The apparatus also includes an excitable tissue control unit operatively connected to at least one of the plurality of electrodes for delivering the non-excitatory signal to the heart. The apparatus further includes a detecting unit operatively connected to a first electrode of the plurality of electrodes for sensing electrical activity in a first cardiac site and for detecting a first electrical depolarization event within the beat cycle. The detection unit is also connected to a second electrode of the plurality of electrodes for sensing electrical activity in a second cardiac site and for detecting at least a second electrical depolarization event within the beat cycle. The apparatus also includes a controller unit operatively connected to the excitable tissue control unit and the detection unit for controlling the operation of the excitable tissue control unit and the detection unit, for receiving from the detection unit signals representing the detection of the first electrical depolarization event and the second electrical depolarization event and for controlling the delivery, through at least one of the plurality of electrodes, of the non-excitatory signal to the second cardiac site or in the vicinity thereof in response to the detecting of the second electrical depolarization event by the detection unit within an alert window period. The alert window period starts at a first delay from the time of detection of the first electrical depolarization event and has a first duration. The applying is delayed from the time of detecting of the second electrical depolarization event. The apparatus also includes a power source for providing power to the excitable tissue control unit, the detection unit and the controller unit.

Furthermore, in accordance with another preferred embodiment of the present invention, the controller is adapted to inhibit the applying of the non-excitatory signal in response to receiving from the detecting unit a signal representing the detecting at the second site of a third electrical depolarization event preceding the second electrical depolarization event. The third electrical depolarization event is detected within an inhibition window period. The inhibition window period starts at a second delay from the time of detection of the first electrical depolarization event and terminates at or before the time of starting of the alert window period. The second delay is smaller than the first delay.

Furthermore, in accordance with another preferred embodiment of the present invention, the controller is adapted for initiating an inhibition refractory period. The inhibition refractory period is initiated by the signal representing the detecting at the second site of the third electrical depolarization event by the detection unit. The inhibition refractory period has a second duration. The controller is adapted for disabling the sensing by the detecting unit of the electrical activity in the second site during the inhibition refractory period.

Furthermore, in accordance with another preferred embodiment of the present invention, the second duration of the inhibition refractory period is a preset duration.

Furthermore, in accordance with another preferred embodiment of the present invention, the second duration of the inhibition refractory period is equal to or larger than the value obtained by summing the inhibition window period, the first duration, the second delay and the maximal allowable duration of the non-excitatory signal.

Furthermore, in accordance with another preferred embodiment of the present invention, the controller is adapted to determine the value of the second duration for the inhibition refractory period from the time of detecting of the third electrical depolarization event within the beat cycle and from the preset values of the first duration of the alert window, the first delay and the maximal allowable duration of the non-excitatory signal.

Furthermore, in accordance with another preferred embodiment of the present invention, the second duration is larger than the value obtained by subtracting the time of detecting of the third electrical depolarization event from the sum of the first delay, the first duration, the second delay and the maximal allowable duration of the non-excitatory signal.

Furthermore, in accordance with another preferred embodiment of the present invention, the detecting unit is adapted for detecting at least one of the first electrical depolarization event and the second electrical depolarization event by using an event detection method selected from a threshold crossing detection method, a detection method based on one or more morphological parameters of the electrical activity, a slope based detection method, and any combination thereof.

Furthermore, in accordance with another preferred embodiment of the present invention, the detecting unit is selected from an analog detecting unit and a digital detecting unit.

Furthermore, in accordance with another preferred embodiment of the present invention, the controller unit is selected from a central processing unit, a micro-controller unit, a digital signal processing unit, a computer, a workstation, and any combination thereof.

Furthermore, in accordance with another preferred embodiment of the present invention, the apparatus further includes an implantable housing. The power unit, the detecting unit, the excitable tissue control unit and the controller unit are contained within the housing.

Furthermore, in accordance with another preferred embodiment of the present invention, the apparatus further includes a telemetry unit disposed within the housing and operatively connected to the controller.

Furthermore, in accordance with another preferred embodiment of the present invention, the plurality of electrodes is implanted within the patient, and the excitable tissue control unit, the detecting unit, the controller unit and the power unit are disposed outside of the patient.

Furthermore, in accordance with another preferred embodiment of the present invention, the first electrode is implanted in or about the right ventricle of the heart and the second electrode is implanted in or about the left ventricle of the heart.

Furthermore, in accordance with another preferred embodiment of the present invention, the first electrode is implanted in or about the right atrium of the heart and the second site is located in or about the left ventricle of the heart.

Furthermore, in accordance with another preferred embodiment of the present invention, the apparatus further includes a pacing unit powered by the power source and operatively connected to at least one of the plurality of electrodes for delivering pacing pulses to the heart. The controller unit is operatively connected to the pacing core unit for controlling the operation thereof.

Furthermore, in accordance with another preferred embodiment of the present invention, the first electrode is implanted in or about the right ventricle of the heart and the second electrode is implanted in or about the left ventricle of the heart.

Furthermore, in accordance with another preferred embodiment of the present invention, the first electrode is operatively connected to the pacing unit for pacing the right ventricle.

Furthermore, in accordance with another preferred embodiment of the present invention, the second electrode is operatively connected to the pacing unit for pacing the left ventricle.

Furthermore, in accordance with another preferred embodiment of the present invention, at least one electrode of the plurality of electrodes is operatively connected to the pacing unit and is implanted in or about the right atrium for pacing the right atrium.

Furthermore, in accordance with another preferred embodiment of the present invention, the first electrode is implanted in or about the right atrium of the heart and the second electrode is implanted in or about the left ventricle of the heart.

Furthermore, in accordance with another preferred embodiment of the present invention, the first electrode is operatively connected to the pacing unit for pacing the right atrium.

Furthermore, in accordance with another preferred embodiment of the present invention, the second electrode is operatively connected to the pacing unit for pacing the left ventricle.

Furthermore, in accordance with another preferred embodiment of the present invention, at least one of the electrodes is implanted in or about the right ventricle of the heart and is operatively connected to the pacing unit for pacing the right ventricle.

Furthermore, in accordance with another preferred embodiment of the present invention, the controller is adapted to control the excitable tissue control unit to deliver the non-excitatory signal in response to the detection of the earliest electrical depolarization event of the second electrical depolarization event within the alert window period.

Furthermore, in accordance with another preferred embodiment of the present invention, the controller is adapted to initiate an alert refractory period in response to the detection of the earliest electrical depolarization event within the alert window period. The alert refractory period starts at the time of detection of the earliest electrical depolarization event within the alert window period and has a third duration. The alert refractory period ends within the duration of the beat cycle. During the alert refractory period, the sensing and the detecting of the detecting unit is disabled.

Furthermore, in accordance with another preferred embodiment of the present invention, the third duration of the alert refractory period is a preset value.

Finally, in accordance with another preferred embodiment of the present invention, the third duration of the alert refractory period is larger than the sum of the first duration, the second delay and the maximal allowable duration of the non-excitatory signal.

BRIEF DESCRIPTION OF THE DRAWINGS

The invention is herein described, by way of example only, with reference to the accompanying drawings, in which like components are designated by like reference numerals, wherein.

DETAILED DESCRIPTION OF THE INVENTION

Notation Used Throughout
The following notation is used throughout this document.

| Term | Definition |
| --- | --- |
| RV | Right ventricle |
| RA | Right atrium |
| LV | Left ventricle |
| SE | Sensed Event |
| PE | Paced Event |
| ETC | Excitable Tissue Control |
| PVC | Premature Ventricular Contraction |
| IEGM | Intra-cardiac Electrogram |
| SVC | Superior Vena Cava |
| GCV | Great Cardiac Vein |
| CS | Coronary Sinus |

-continued

Notation Used Throughout
The following notation is used throughout this document.

| Term | Definition |
|------|------------|
| CHF | Congestive Heart Failure |
| PAC | Premature Atrial Contraction |

Typically, ETC signal delivery is timed relative to a sensed signal representing the depolarization wave locally sensed at or near the site of the electrodes used for ETC signal delivery. This signal may be a biphasic or polyphasic intra-cardiac electrogram (IEGM) signal sensed by a lead or catheter including one or more electrodes capable of sensing an IEGM signal and of delivering pacing pulses. The depolarization wave represented by the IEGM is an electrical event caused by spreading myocardial electrical excitation evoked by the natural pacemaker of the heart (normally the Sino-atrial node) in which case the event is referred to as a sensed event (SE), or by a pacing pulse delivered to the myocardium, in which case the event is referred to as a paced event (PE). The IEGM signal may also include electrical depolarizations caused by ectopic myocardial activation such as a premature atrial contraction (PAC) or a premature ventricular contraction (PVC). Furthermore, the IEGM signal may include artifacts caused by electrical noise.

Figure 1:
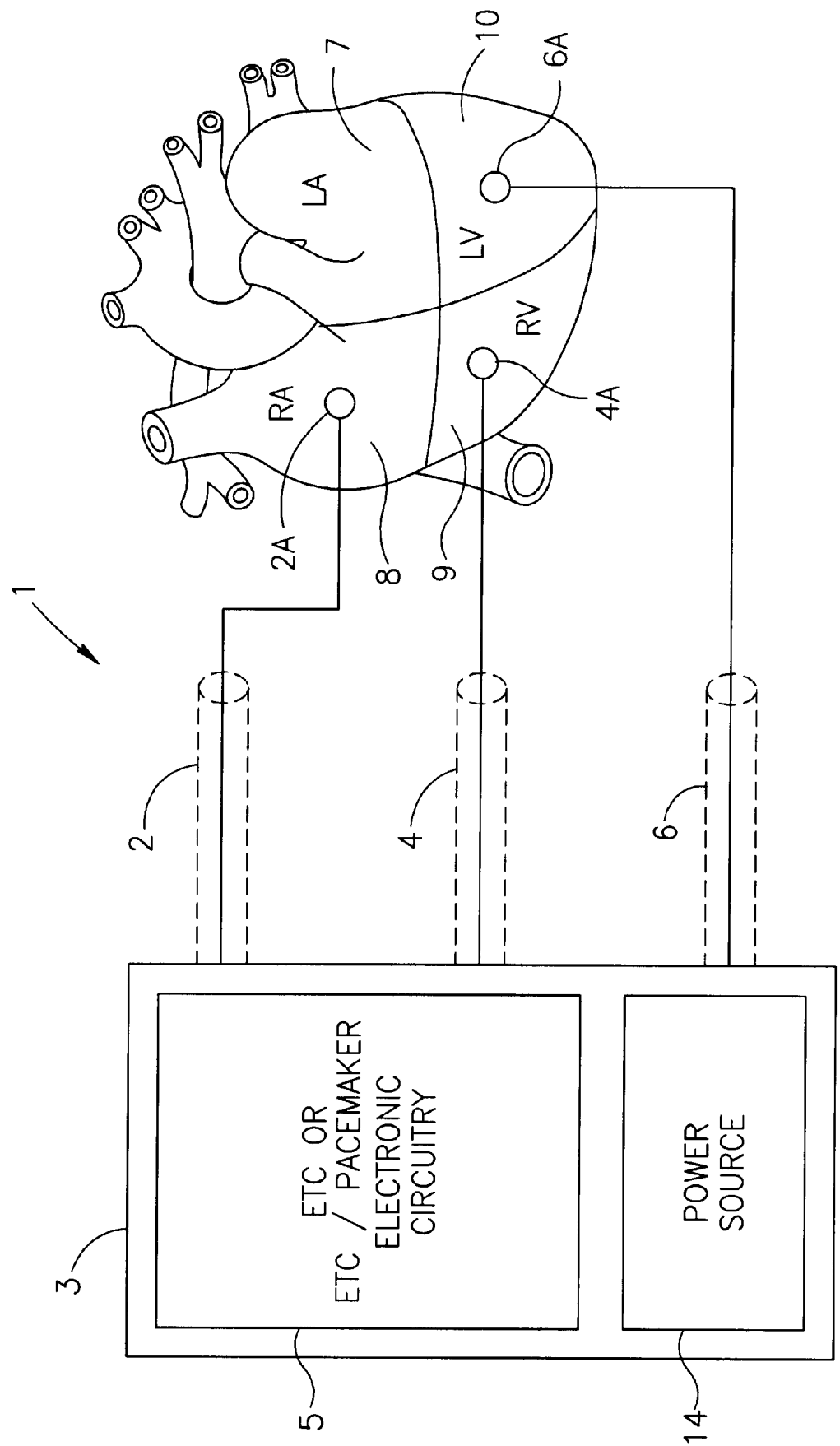
FIG. 1 is a schematic diagram representing a typical lead placement configuration of an ETC device for delivering ETC non-excitatory signals to the heart, in accordance with a preferred embodiment of the present invention.

Reference is now made to FIG. 1 which is a schematic diagram representing a typical lead placement configuration of an ETC device for delivering ETC non-excitatory signals to the heart, in accordance with a preferred embodiment of the present invention. The device 1 may be an ETC device capable of delivering non-excitatory ETC signals to the heart, or an ETC/pacemaker device capable of delivering non-excitatory ETC signals to the heart and of pacing the heart if necessary. The device 1 includes an implantable housing or case 3 for housing the electronic circuitry 5 of the ETC or ETC/pacemaker device (not shown in detail in FIG. 1) of the device 1 which is illustrated in detail hereinafter. The device 1 also includes a power source 14 for powering the circuitry 5 as is known in the art and disclosed in detail hereinafter. A pacing/sensing lead 2 is suitably connected to the case 3 and operatively connected to the circuitry 5.

The lead 2 includes an electrode 2A applied to the right atrium (RA) 8. The electrode 2A is used for sensing SEs and for delivering pacing pulses if necessary. The left atrium 7 (LA) is also shown in FIG. 1. The pacing lead 2 may be inserted into the RA 8 through the sub-clavian vein and the superior vena cava (SVC), but other methods of insertion are also possible. Another pacing/sensing lead 4 is connected to the case 3 and operatively connected to the circuitry 5. The lead 4 includes an electrode 4A which is applied the right ventricle (RV) 9 and is used for sensing right ventricular SEs and PEs and for delivering pacing pulses if necessary. The lead 4 may be inserted into the RV through the subclavian vein and the superior vena cava (SVC), but other methods of insertion are also possible. A third lead 6 is also suitably connected to the case 3 and operatively connected to the circuitry 5. The lead 6 includes an electrode 6A which is applied to the wall of a lateral vein of the great cardiac vein (GCV) and is used for local sensing of SEs and PEs in the left ventricle (LV) 10 and for delivering non-excitatory ETC signals to the LV 10 if required.

The lead 6 may be inserted through the sub-clavian vein, passing through the SVC, the right atrium, the coronary sinus (CS) and the GCV and reaching a lateral vein of the GCV, but other methods of insertion of the leads 6 into or about the left ventricle (LV) are also possible. The implantable case 3 is typically implanted in a thoracic sub-cutaneous pocket (not shown), but other implantation positions are also possible. It is noted that the above disclosed lead placements and insertion paths and the case placement are given by way of example only and that other electrode placements and lead insertion paths and case placements are also possible.

It is noted that while each of the single electrodes 2A, 4A and 6A of the device 1 of FIG. 1 may be used for sensing with respect to a common reference point such as the case 3 of the device 1, other preferred embodiments of the present invention may use pairs of locally applied electrodes (not shown) which may be used for local differential sensing. For example, The lead 2 may include a pair of electrodes (not shown) which are applied to the RA 8 for local sensing, the lead 4 may include a pair of electrodes (not shown) which are applied to the RV 9 for local sensing and the lead 6 may include a pair of electrodes (not shown) which are applied to the LV 10 for local sensing.

It is further noted that while the electrode 2A of the lead 2 is used for both sensing and pacing the RA 8, in other preferred embodiments of the present invention the lead 2 may include additional electrodes or electrode pairs (not shown) such that one or more electrode or electrode pair is used for sensing in the RA 8 while other separate electrode (s) or electrode pairs are used for pacing the RA 8. Similarly, in accordance with a preferred embodiment of the present invention, The lead 4 may include more than one electrode or pair of electrodes (not shown) which may be separately used for sensing and for pacing the right ventricle 9. Yet similarly, the lead 6 may include more than one electrode or electrode pairs (not shown) of which one or more electrode or electrode pair is used for sensing in the left ventricle 10 and one or more additional electrodes or electrode pairs are used for delivering non-excitatory ETC signals to the left ventricle 10.

It will therefore be appreciated by those skilled in the art, that the number and arrangement of the electrodes within the leads 2, 4 and 6 may be varied in many ways and many combinations all being within the scope and spirit of the present invention.

Various types of electrodes and electrode positioning methods known in the art may be used for sensing and pacing and for delivering ETC signals to the heart. One or more of the electrodes or electrode pairs 2A, 4A and 6A may be implanted within a cardiac chamber and placed in contact with the endocardium as disclosed hereinabove. One or more of the electrodes or electrode pairs 2A, 4A and 6A may also be disposed within a cardiac blood vessel, such as a lateral vein of the GCV or another suitable cardiac blood vessel, and used for sensing and/or pacing and/or delivering ETC signals to the myocardial tissue adjacent to or in contact with the blood vessel wall. One or more of the electrodes or electrode pairs 2A, 4A and 6A may also be epicardial electrodes which may be epicardially applied to the heart as is well known in the art.

Typically, ETC signals are delivered to the left ventricle via the electrode(s) 6A of lead 6. The timing of the ETC signal is triggered by locally sensing in the LV the depolarization wave of the PE or the SE, using the sensing/pacing electrode(s) 6A of the lead 6. The sensing/pacing electrode (s) 6A of the lead 6 is also used as the ETC delivery electrode.

To facilitate correct timing of the ETC delivery, measures need to be taken so that ETC signal delivery is not triggered by local LV sensing of noise, premature ventricular contractions (PVCs), premature atrial contractions (PACs) or by delayed sensing of remote events such as a right ventricular depolarization. One possible approach is the restricting of the local sense triggering for ETC delivery to a predefined time window.

The use of a predefined time window for other different purposes such as to detect activation for capture verification in pacemakers is known in the art. U.S. Pat. No. 5,443,485 to Housworth et al. discloses the use of a timing window to detect a paced stimulation pulse for achieving capture verification to ensure that the pacing pulse energy is high enough.

U.S. Pat. No. 5,683,431 to Wang discloses a method for performing pacemaker capture verification using electrodes different than the pacing electrodes to sense the activation evoked by the pacing pulse.

U.S. Pat. No. 5,391,192 to Lu et al. discloses a method for externally determining the minimum energy of a pacing pulse for capture verification using window based detection of activation.

Figure 2:
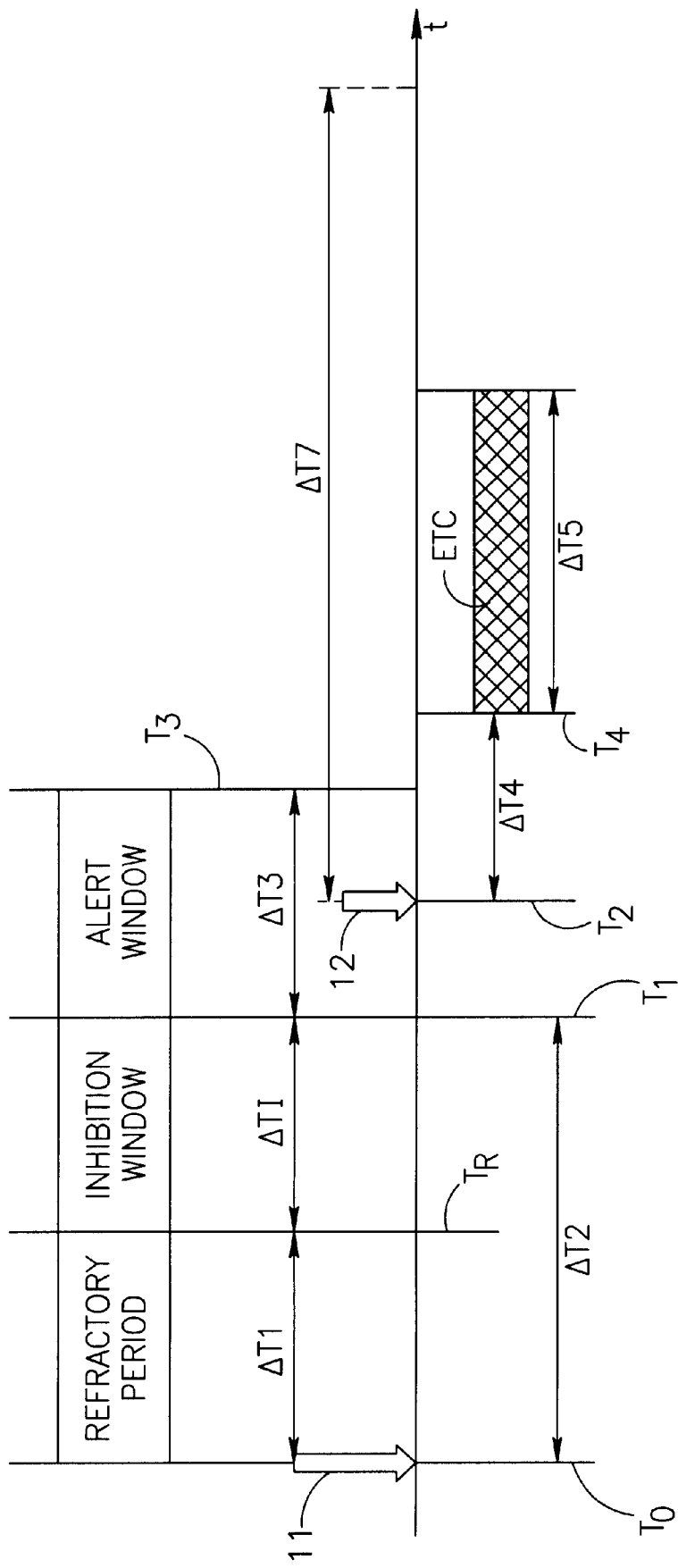
FIG. 2 is a schematic diagram useful in understanding the method of using an alert window for timing the delivery of ETC signals useful in operating the device of FIG. 1, in accordance with a preferred embodiment of the present invention.

Reference is now made to FIG. 2 which is a schematic diagram useful in understanding a method using an alert window for timing the delivery of ETC signals useful in operating the device of FIG. 1, in accordance with a preferred embodiment of the present invention. The detection time window is referred to as the "alert window" throughout the present application.

The horizontal axis of FIG. 2 represents time. The arrow labelled 11 schematically represents the timing of a depolarization event 11 locally sensed in the RV by one or more electrodes (not shown) of the lead 4 of FIG. 1. The time $T_0$ represents the time of detection of the RV event. Typically, the time $T_0$ represents the time point at which a threshold crossing occurs. However, $T_0$ may also represent the time of event detection obtained by other methods known in the art for cardiac event detection such as detection methods based on the shape of the signal (also known as signal morphology based detection methods) or other suitable detection methods known in the art. The RV event 11 may represent a locally sensed RV depolarization initiated by a naturally occurring SA node evoked atrial event (not shown) or initiated by artificial atrial pacing. The RV event 11 may also represent a locally sensed RV depolarization initiated by a pacing pulse delivered to the RV through an electrode (not shown) included in the lead 4 of FIG. 1. After the time $T_0$, a local sense "refractory" period labeled $\Delta T1$ begins. The refractory period $\Delta T1$ ends at time $T_R$. During the refractory period $\Delta T1$ no sensing is performed. This refractory period is used to avoid the electrical pacing artifact due to electrode polarization and/or electrode cross-talk. The refractory period may also be useful in avoiding electrical artifacts due to far field sensing as is well known in the art.

Typically, the duration of the refractory period $\Delta T1$ is approximately 10–15 milliseconds but other values may be used depending, inter alia, on the specific application, electrode type, and detection method used. It is noted that, in accordance with one preferred embodiment of the present invention, the value of the refractory period duration may be set to $\Delta T1=0$. In such an embodiment no refractory period $\Delta T1$ is implemented.

A local sense alert window having a duration $\Delta T3$ starts at time $T_1$ and ends at time $T_3$. The time interval between time points $T_0$ and $T_1$ is defined as the alert window delay interval $\Delta T2$ which is the delay between time of detection of the depolarization event 11 and the beginning of the alert window $\Delta T3$.

The arrow labeled 12 of FIG. 2 schematically represents the occurrence of a depolarization event locally sensed in the LV. For example, the locally sensed event 12 may be sensed by a sensing electrode (not shown) or by an ETC signal delivery electrode (not shown) included within the lead 6 of FIG. 1. The time $T_2$ represents the time of detection of the LV depolarization event 12. Typically, the time $T_2$ represents the time point at which a threshold crossing occurs as is disclosed hereinbelow. However, $T_2$ may also represent the time of event detection obtained by other methods known in the art for cardiac event detection.

An article titled "NEURAL NETWORK BASED ADAPTIVE MATCHED FILTERING FOR QRS DETECTION" by Xue et al., published in IEEE Transactions on Biomedical engineering, Vol. 39, No. 4 pp. 317–329 (1992) and incorporated herein by reference, discloses an adaptive matched filtering algorithm based on an artificial neural network for QRS detection.

An article titled "IDENTIFICATION OF VENTRICULAR TACHYCARDIA WITH USE OF THE MORPHOLOGY OF THE ENDOCARDIAL ELECTROGRAM" by Langberg et al., published in Circulation, Vol. 77, No. 6 pp. 1363–1369 (1988) and incorporated herein by reference, discloses the application of a template to derive morphological parameters of unipolar and bipolar electrogram signals for detecting tachycardia.

An article titled "CLASSIFICATION OF CARDIAC ARRHYTHMIAS USING FUZZY ARTMAP" by F. M. Ham and S. Han, published in IEEE Transactions on Biomedical engineering, Vol. 43, No. 4 pp. 425–430 (1996) and incorporated herein by reference, discloses the use of a fuzzy adaptive resonance theory mapping (ARTMAP) neural net classifier for classifying QRS complexes under normal and abnormal conditions.

U.S. Pat. No. 5,782,876 to Flammang titled "METHOD AND APPARATUS USING WINDOWS AND AN INDEX VALUE FOR IDENTIFYING CARDIAC ARRHYTHMIAS", incorporated herein by reference, discloses the use of the sensed electrogram slope (derivative of ECG) for morphological electrogram detection in a device for identifying cardiac arrhythmias.

The above referenced morphological signal detection methods, as well as other signal morphology based detection methods known in the art, may be adapted for detection of the depolarization events within the IEGM signals of the present invention.

The detection of the LV sensed event 12 at time $T_2$ triggers the delivery of an ETC signal represented by the cross hatched area labeled ETC. The ETC signal starts at a time point $T_4$ separated from $T_2$ by a delay interval $\Delta T4$. The ETC signal has a duration $\Delta T5$.

Preferably, the value of the duration of the ETC signal $\Delta T5$ is a variable duration and may vary from one beat cycle to another in accordance with the required modification of myocardial contractility. Typically, the duration and or other parameters of the ETC signal may be modified based on the current value of the heart rate. The methods for determining the required ETC signal duration $\Delta T5$ are not the subject matter of the present invention and will not be disclosed in detail hereinafter.

It is noted that, in accordance with other preferred embodiments of the present invention, the duration of the ETC signal $\Delta T5$ may be a constant value which does not vary from one beat cycle to another beat cycle.

The ETC signals may have various waveforms, durations and intensities as disclosed in detail by Ben Haim et al. in the above referenced International Publications No. WO 97/25098, WO 98/10828, WO 98/10829, WO 98/10830, WO 98/10831 and WO 98/10832. The characteristics of the delivered ETC signals are not the subject of the present invention and will not be further discussed hereinafter.

Only a locally sensed depolarization event detection occurring within the duration of the alert window $\Delta T3$ is used to trigger an ETC signal. The detection of an electrical depolarization event happening outside the alert window will not result in triggering of an ETC signal. This has the advantage of reducing the probability of delivering an improperly timed ETC signal due to electrical noise occurring outside the preset duration of the alert window $\Delta T3$. However, if a depolarization event (not shown) due to an ectopic beat is detected between the time $T_0$ and the time $T_1$ in a case where the refractory period $\Delta T1$ is not used, or between the time $T_R$ and the time $T_1$ in a case where the refractory period $\Delta T1$ is used, and then a later depolarization event (not shown) is detected within the duration of the alert window $\Delta T3$, the triggering of an ETC signal by the later occurring depolarization event may result in an improperly timed ETC signal. Therefore, in order to prevent such improper timing, the timing method may further include an inhibitory window $\Delta TI$. Any depolarization event which is detected within the duration of the inhibition window $\Delta TI$ will result in the inhibiting of ETC signal delivery within the current beat cycle as disclosed in detail hereinbelow.

In accordance with one preferred embodiment of the present invention, $\Delta TI = \Delta T2 - \Delta T1$, in such a preferred embodiment the inhibition window $\Delta TI$ starts at the end of the refractory period $\Delta T1$ and ends at the beginning of the alert window $\Delta T3$. If no refractory period is used ($\Delta T1=0$), the inhibition window spans the entire alert window delay interval $\Delta T2$. However, in accordance with other preferred embodiments of the timing method of present invention, the end of the inhibition period $\Delta TI$ may be separated from the beginning of the alert window $\Delta T3$ by an intermediate time interval (not shown in FIG. 2 for the sake of clarity of illustration). The detection of a depolarization event within the duration of such an intermediate time interval will not result in the inhibition of triggering of an ETC signal by a later depolarization event detected within the duration of the alert window $\Delta T3$.

If a depolarization event was detected in the IEGM signal which is locally sensed in the left ventricle 10 within the duration of the inhibition window $\Delta TI$, ETC signal delivery is inhibited such that later occurrence of a depolarization event within a preset "inhibition refractory period" (not shown in FIG. 2 for the sake of clarity of illustration) of the current beat cycle will not result in a delivery of an ETC signal. This feature has the advantage that it reduces the probability of erroneous detection of spurious noise or of ectopic beats such as PVCs or PACs and the subsequent triggering of the delivery of an incorrectly timed ETC signal. The details of the implementation of the inhibition refractory period are disclosed in detail hereinafter (with reference to FIG. 7)

Typically, the local sensing sensitivity is adjusted such that, only events of a certain amplitude will be detected. This is achieved by setting a detection threshold. Threshold crossing detection methods for electrical signals are well known in the art and are not the subject matter of the present invention. Such threshold crossing detection methods are commonly used in pacemakers for sensed event detection.

Briefly, any acceptable detection method based on threshold crossing of one or more threshold levels may be used with the present invention. For example, the sensed electrogram may be biphasic, and two threshold levels may be used including a positive threshold level and a negative threshold level. Alternatively, full wave rectification of the electrogram may be used to obtain a signal which is positive only, such that a single positive threshold level may be used. Additionally, other methods of detection may be used which are based on signal morphology as disclosed in detail hereinabove.

Since multiple threshold crossings may occur during the same depolarization event or during noise signals, ambiguity may arise as to which threshold crossing should be used as the trigger. This may be solved by triggering by the first threshold crossing in the window and by implementing an "alert refractory period" $\Delta T7$ following the first threshold crossing of the LV sensed event 12 at time $T_2$ to prevent multiple triggering by multiple threshold crossings occurring within a single depolarization wave representing a single event. The alert refractory period $\Delta T7$ starts at the time $T_2$ and has a fixed duration represented by the double headed arrow labeled $\Delta T7$. During the alert refractory period $\Delta T7$ no sensing is performed so that additional triggering cannot happen during the period $\Delta T7$.

It is noted that, since the first threshold crossing due to an LV sensed event 12 may happen at any time during the alert window $\Delta T3$, and since the duration of the ETC signal $\Delta T5$ may be varied from one beat cycle to another (for varying the effects of the ETC signal on myocardial contraction), the duration of the alert refractory period $\Delta T7$ is set such that it is larger than the sum of the durations of the alert window $\Delta T3$, the delay interval $\Delta T4$ and the maximal allowable duration $\Delta T5_{MAX}$ of the ETC signal. The maximal allowable duration $\Delta T5_{MAX}$ is a preset value.

Thus, $\Delta T7 > \Delta T3 + \Delta T4 + \Delta T5_{MAX}$. This ensures that no further threshold crossings will be sensed and detected after the first threshold crossing detection until the ETC signal has ended, irrespective of the time of occurrence of the first threshold crossing detection $T_2$ within the alert window duration $\Delta T3$ and of the specific duration $\Delta T5$ of the ETC signal delivered within the current beat cycle.

Typically, the duration $\Delta T3$ of the alert window is approximately 30 milliseconds, the duration of the delay interval $\Delta T4$ is approximately 60 milliseconds and the maximal allowable duration $\Delta T5_{MAX}$ of the ETC signal is approximately 20–30 milliseconds. However, other values of $\Delta T3$, $\Delta T4$ and $\Delta T5_{MAX}$ may be used.

A typical value of the duration of the alert refractory period $\Delta T7$ is therefore approximately 150–200 milliseconds. However, other values of the duration of the alert refractory period $\Delta T7$ may be used depending, inter alia, on the particular values of $\Delta T3$, $\Delta T4$ and $\Delta T5_{MAX}$ used. The duration of the alert refractory period $\Delta T7$ is a preset value and does not change from one beat cycle to another. However, The duration of the alert refractory period $\Delta T7$ may be changed if necessary by appropriately reprogramming the software embedded within the device 1 telemetrically or non-telemetrically (depending on the specific hardware implementation of the device 1).

For the sake of simplicity, the method of the present invention will be disclosed as using a single positive threshold level. A certain positive threshold voltage level is set for the pacemaker/ETC device. A crossing of this threshold level by the IEGM signal occurring within the time interval between $T_R$ and $T_3$ will be detected as an event. For example, the detection threshold may be set as +3.0 millivolts but other suitable threshold levels may be used for detection.

Figure 3:
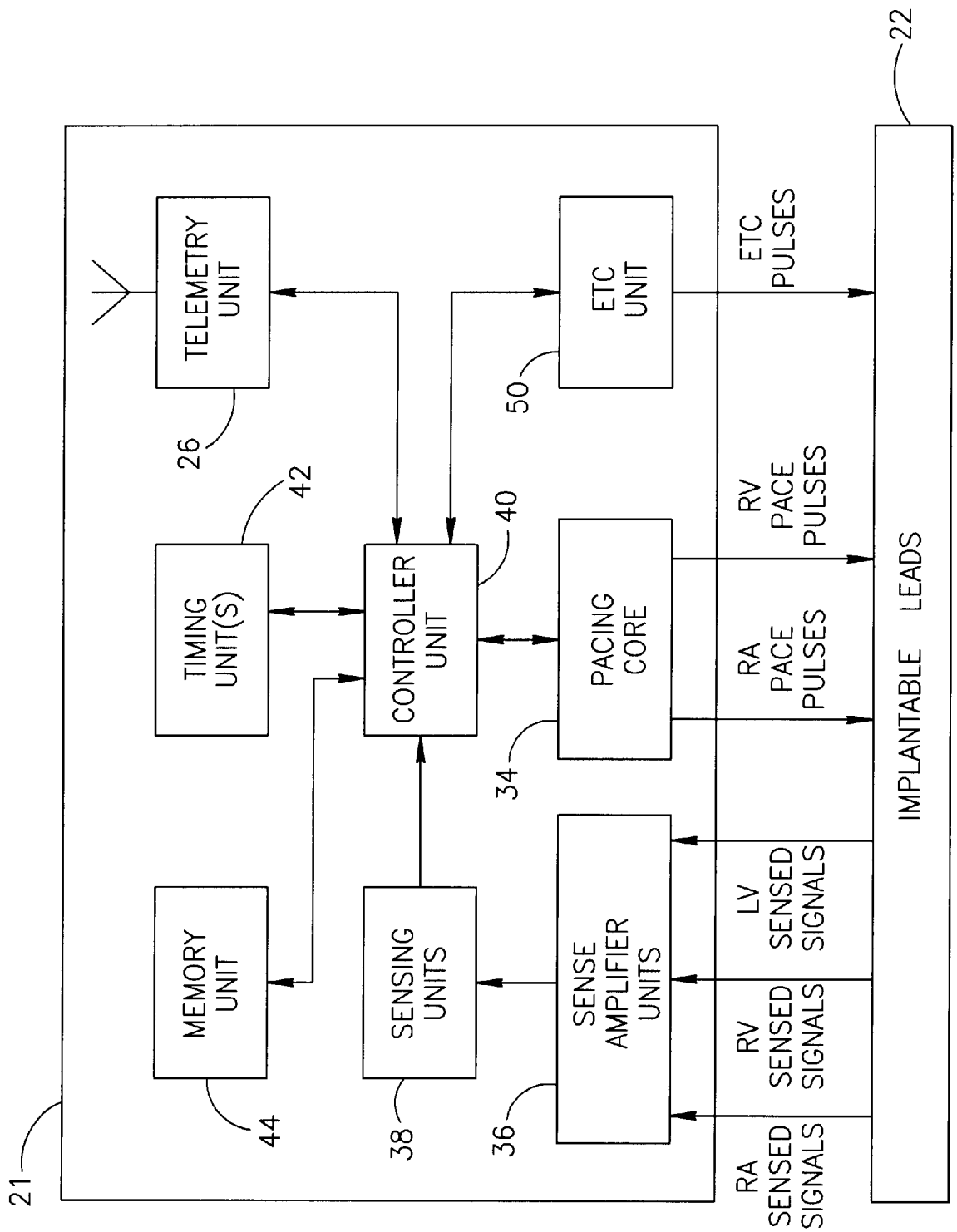
FIG. 3 is a schematic functional block diagram illustrating an implantable device 21 for pacing the heart and for delivering ETC signals to the heart using the method of timing of the non excitatory signal, in accordance with a preferred embodiment of the present invention.

Reference is now made to FIG. 3 which is schematic functional block diagram illustrating an implantable device 21 for pacing the heart and for delivering ETC signals to the heart using the method of timing of the non excitatory signal, in accordance with a preferred embodiment of the present invention. The implanted pacemaker/ETC device 21 includes a pacing core 34 for providing pacing pulses to the RA and RV pacing electrodes (not shown) of the implantable leads 22. The pacemaker/ETC device 21 further includes sense amplifier units 36 for amplifying the RA, RV and LV signals locally sensed by the sensing electrodes (not shown) of the implantable leads 22. For example, when the pacemaker/ETC device 21 represents the pacemaker/ETC device 1 of FIG. 1, one of the sense amplifier units 36 receives the signal locally sensed in the RA 8 from lead 2 of FIG. 1, another of the sense amplifier units 36 receives the signal locally sensed in the RV 9 from lead 4 of FIG. 1 and a third one of the sense amplifier units 36 receives the signal locally sensed in the LV 10 from the lead 6 of FIG. 1.

The pacemaker/ETC device 21 further includes sensing units 38 suitably connected to a controller unit 40. The sensing units 38 receive the amplified locally sensed signals from the amplifier units 36 and provide trigger signals to the controller unit 40 for activating the pacing core as is known in the art. The pacemaker/ETC device 21 further includes timing units 42, connected to the controller unit 40 for providing the controller unit 40 with clock signals, and a memory unit 44 suitably connected to the controller unit 40. The controller 40 can store data in the memory unit 44 and can access the data stored in the memory unit 44 for processing the accessed data and/or for sending data to a telemetry unit 26 for telemetrically communicating the data to a receiving station (not shown) placed outside of the patient. The memory unit 44 may include random access memory (RAM) units (not shown), read only memory (ROM) units (not shown), other suitable type of memory units known in the art, or any suitable combination of memory unit types.

It is noted that the pacemaker/ETC device 21 when connected to implantable leads having the configuration of leads 2, 4, and 6 of FIG. 1, may function, inter alia, as a pacemaker in a DDD mode, including, inter alia, the ability to detect PVCs as is known in the art.

The telemetry unit 26 is used for wirelessly transmitting data stored in memory unit 44 under the control of the controller unit 40. The pacemaker/ETC device 21 further includes an excitable tissue controller (ETC) unit 50. The ETC unit 50 is suitably connected to the controller unit 40 and to one or more ETC electrodes (not shown) within the leads 22. For example, when the pacemaker/ETC device 21 represents the pacemaker/ETC device 1 of FIG. 1, the ETC unit 50 is connected to the ETC signal delivering electrode 6A of the lead 6 of FIG. 1. However, in other preferred embodiments of the present invention, the ETC unit 50 may be connected to one or more ETC electrodes or ETC electrode pairs (not shown) which are used for delivering ETC signals. The controller unit 40 controls the delivery of ETC signals to the myocardium by timing the delivery of suitable control signals to the ETC unit 50.

Figure 4:
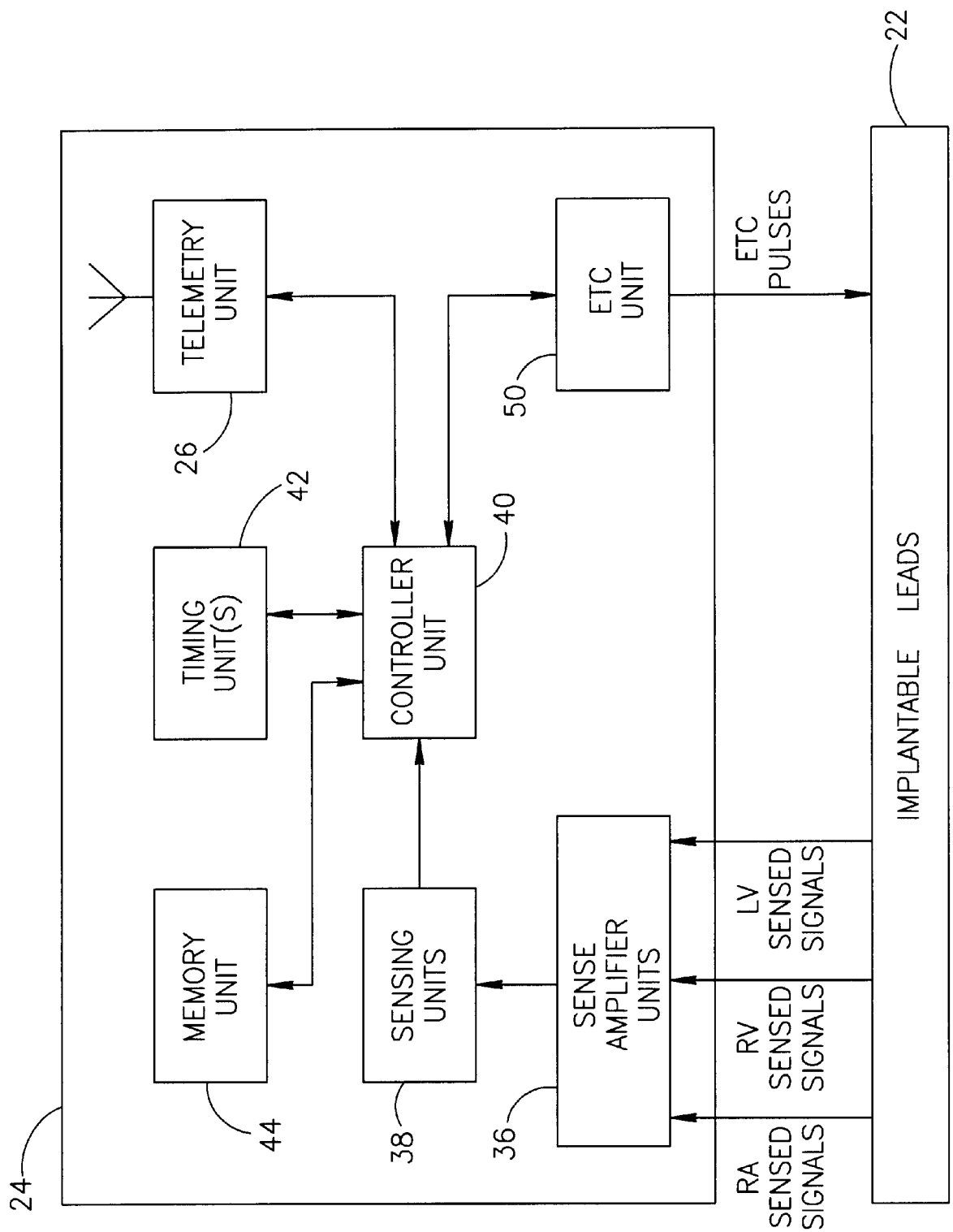
FIG. 4 is a schematic functional block diagram illustrating an implantable device for delivering ETC signals to the heart using the method of timing of the non excitatory signal, in accordance with a preferred embodiment of the present invention.

Reference is now made to FIG. 4 which is schematic functional block diagram illustrating an implantable device for delivering ETC signals to the heart using the method of timing of the non excitatory signal, in accordance with a preferred embodiment of the present invention. The device 24 is similar to the device 21 of FIG. 3, except that it does not include the pacing core 34 of the device 21 of FIG. 3.

The device 24 may be used in patients where ETC signals need to be delivered to the heart but pacing of the heart is not required, such as but not limited to congestive heart failure (CHF) patients. CHF patients may have an unimpaired cardiac conduction system and may exhibit no chronotropic incompetence and no conduction abnormalities or blocks. In the cases where the device 24 is used for delivering ETC signals to the heart, the electrodes (not shown) in the implantable leads 22 are used for sensing and for delivering ETC signals and are not used for pacing the heart.

Figure 5:
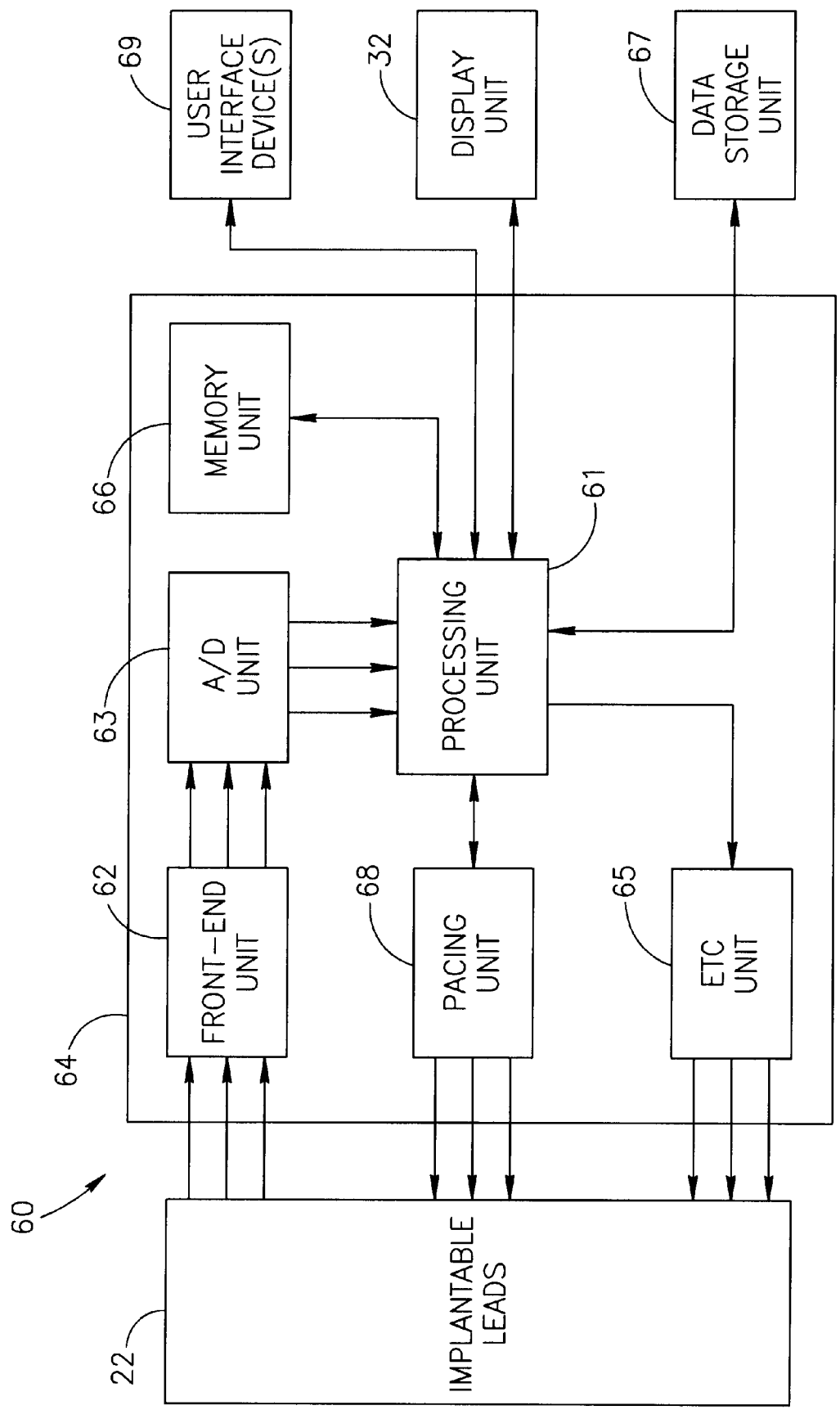
FIG. 5 is a schematic functional block diagram illustrating a system including a non-implanted device and implantable electrodes for pacing the heart and for delivering ETC signals to the heart using the method of timing of the non excitatory signal, in accordance with a preferred embodiment of the present invention.

Reference is now made to FIG. 5 which is schematic functional block diagram illustrating a system including a non-implanted device and implantable electrodes for pacing the heart and for delivering ETC signals to the heart using the method of timing of the non excitatory signal, in accordance with a preferred embodiment of the present invention. The system 60 includes a plurality of implantable leads 22 implanted within a patient (the patient is not shown) and an external ETC device 64. The plurality of implantable leads 22 may include, for example, the leads 2, 4 and 6 of FIG. 1. However, the plurality of leads 22 may include any other suitable combinations of leads including a plurality of sensing, pacing and ETC electrodes (not shown in detail) positioned in two or more chambers of the heart as disclosed for the devices 1, 21 and 24 hereinabove.

The plurality of leads 22 are implanted in the patient's heart and are then suitably connected to the ETC device 64 which includes the necessary electronic circuitry for sensing electrical activity in the heart, for pacing the heart if necessary and for delivering ETC non-excitatory signals to the heart using the method of timing the delivery of ETC signals to the heart in accordance with the method of the present invention, as disclosed in detail hereinabove and illustrated if FIG. 2.

The ETC device 64 includes a processing unit 61, a front-end unit 62, an analog to digital converting unit (A/D) 63, a pacing unit 68 and an ETC unit 65. The front end unit 62 is suitably connected to one or more of the sensing electrodes of the leads 22 and to the processing unit 61 for pre-conditioning one or more IEGM signals sensed by these one or more sensing electrode. The front-end unit 62 may include suitable circuitry such as one or more amplifier circuits (not shown) for amplifying the IEGM signals sensed by the one or more sensing electrodes. The front-end unit 62 may also include filter circuits (not shown) for filtering the amplified signals prior to digitizing them by the A/D unit 63. The front-end unit 62 is suitably connected to the AND unit 63 and provides amplified or amplified and filtered IEGM signals thereto for digitizing.

The A/D unit 63 may include one or more separate A/D converters (not shown) each A/D converter being dedicated to a single sensing electrode of the one or more sensing electrodes included within one or more of the leads 22. Alternatively, the A/D unit 63 may include a single A/D converter (not shown) suitably connected to a plurality of sensing electrodes of the leads 22 through a multiplexer unit (not shown). The digitized IEGM signals are provided to the processing unit 61 by the A/D unit 63 for further processing. The processing unit 61 digitally performs the detection of events based on the digitized IEGM data provided by the A/D unit 63. The ETC device 64 further includes a memory unit 66 suitably connected to the processing unit 61 for storing data.

The pacing unit 68 is suitably connected to the processing unit 61 and to one or more pacing electrodes of the leads 22. The pacing unit 68 receives control signals from the processing unit 61 for controlling the delivery of pacing pulses to one or more locations in the heart (not shown). The pacing unit 68 includes all the necessary circuitry for delivering pacing pulses to one or more pacing electrodes. Such circuitry is well known in the art and is not shown in detail hereinafter.

It is noted that the ETC device 64 when connected to the implantable leads 22 is capable of performing all the functions of an implanted pacemaker. For example, when the leads 22 have the configuration of leads 2, 4, and 6 of FIG. 1, the ETC device 64 is capable of performing, inter alia, all the functions of an implanted pacemaker in a DDD mode. These functions include, inter alia, the ability of detection of PVCs as is well known in the art.

The ETC unit 65 is suitably connected to the processing unit 61 and to one or more ETC signal delivery electrodes of the implantable leads 22. The ETC unit 65 receives control signals from the processing unit 61 for controlling the delivery of ETC signals to the heart through the one or more ETC delivery electrodes of the implantable leads 22. The ETC unit 65 may be any suitable unit for delivering ETC signals to the myocardium as disclosed by Ben Haim et al. in the above referenced International Publications No. WO 97/25098, WO 98/10828, WO 98/10829, WO 98/10830, WO 98/10831 and WO 98/10832.

The system 60 further includes a display unit 32 suitably connected to the processing unit 61 for displaying graphic symbolic and numerical data processed by the processing unit 61. The data may be presented to the physician or user operating the system 60. The system 60 may further include a data storage unit 67 for storing data. The data storage unit 67 may be any suitable data storage device for storing data on a storage medium such as a magnetic storage medium, an opto-magnetic storage medium, an optical storage medium, a holographic storage medium or any other type of fixed or removable storage medium. Some non-limiting examples of the storage device 67 are, a magnetic hard disk drive, a magnetic floppy disk drive, an opto-magnetic disk drive, an optical disc drive. The data stored on the data storage device 67 may include, inter alia, patient clinical data, patient demographic data, various IEGM data, data including the alert window parameters and any other relevant or desired data. The data storage device 67 may be used for storing data for a plurality of different patients.

The system 60 further includes one or more user interface devices 69 suitably connected to the processing unit 61 through a suitable communication interface (not shown) for enabling the user of the system 60 to input data and commands for controlling the sensing, pacing and ETC signal delivery operation of the ETC device 64. The user interface device(s) 69 may be a keyboard, a pointing device such as a mouse, a light pen in combination with a suitable touch sensitive screen or tablet, or the like or any other suitable device for inputting data or commands to the ETC device 64, or any suitable combination thereof.

In operation after the leads 22 are implanted in the heart of the patients and are connected to the ETC device 64, the ETC device 64 is operative to pace the heart if necessary, and to perform the sensing of IEGM signals and the delivery of ETC signals to the heart using the method for determining the timing of delivery of ETC signals using an alert window and/or inhibition window disclosed in detail hereinabove and illustrated in FIG. 2. It is noted that the ETC device 64 is capable of performing all the activities of an implanted pacemaker/ETC device such as the pacemaker/ETC device 21 of FIG. 3 except for the telemetry functions. The ETC device 64 may perform cardiac pacing at one or more cardiac locations and may controllably deliver ETC signals to one or more cardiac locations. The performance of the functions of a pacemaker/ETC device by the ETC device 64 may be achieved by using different methods and/or different hardware implementation than the methods and hardware of an implantable pacemaker/ETC device, such as the pacemaker/ETC device 21 of FIG. 3. For example, while in the pacemaker/ETC device 21 the event detection is performed by sensing units 38 which are analog circuits, the event detection in the ETC device 64 is performed by digitally processing the digitized IEGM data provided by the A/D unit 63. Additionally, the pacing unit 68 and the ETC unit 65 may have hardware and software implementations different than those of the pacing core 34 and the ETC unit 50, respectively, of the pacemaker/ETC device 21 because of the physical size and current consumption limitations imposed on the design of the pacing core 34 and the ETC unit 50 of the pacemaker/ETC device 21 due to the dimensional limitations imposed in an implanted device. These limitation are not relevant in the non-implanted ETC device 64. However, functionally, the sensing, pacing and ETC delivery of the ETC device 64 are similar to, and may be regarded as simulating the same functions of an implanted of the pacemaker/ETC device, such as, for example, the functions of the pacemaker/ETC device 21 of FIG. 3.

Figure 6:
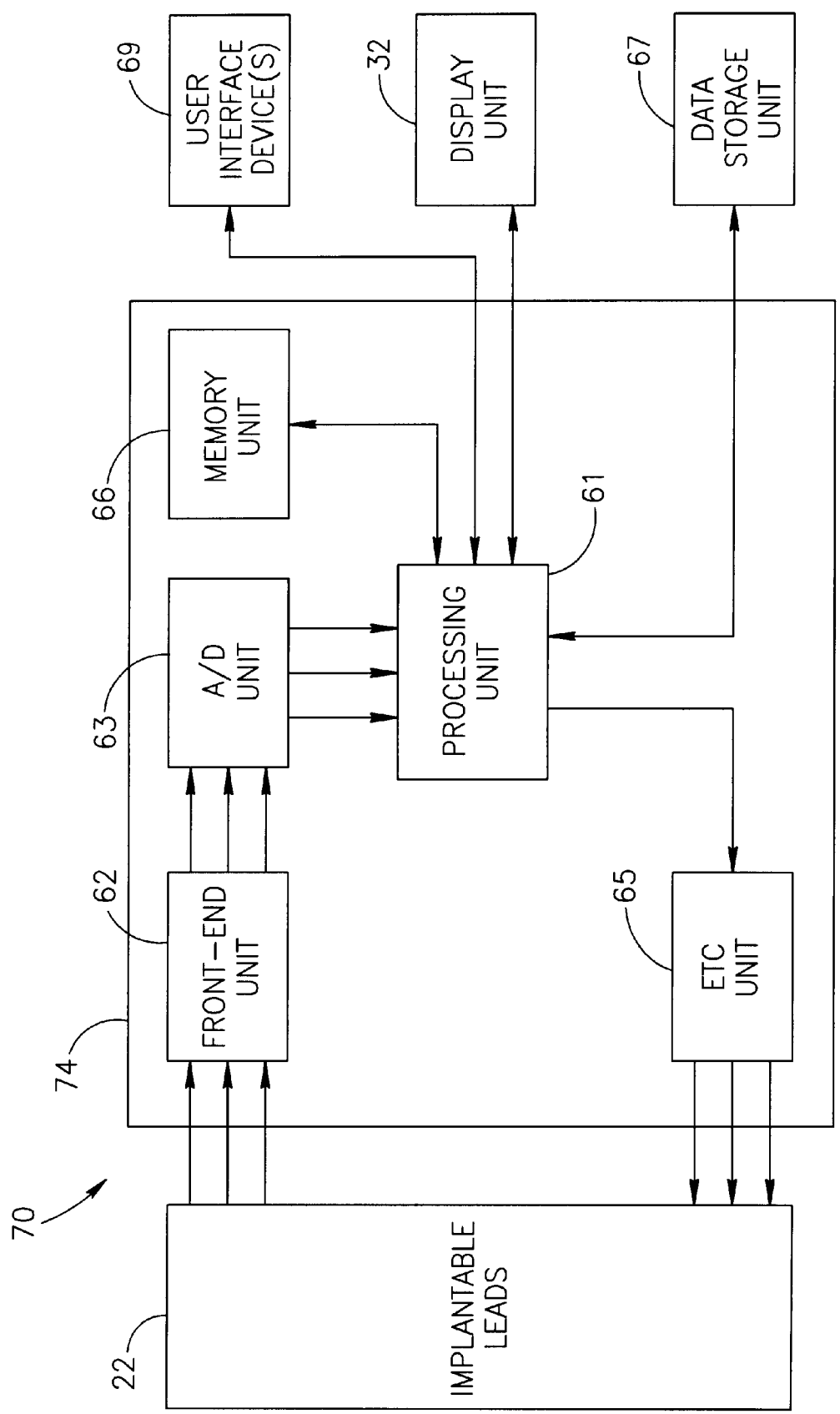
FIG. 6 is a schematic functional block diagram illustrating a system 70 including a non-implanted device having implantable electrodes for delivering ETC signals to the heart using the method of timing of the non excitatory signal, in accordance with a preferred embodiment of the present invention.

Reference is now made to FIG. 6 which is schematic functional block diagram illustrating a system 70 including a non-implanted device having implantable electrodes for delivering ETC signals to the heart using the method of timing of the non excitatory signal, in accordance with a preferred embodiment of the present invention.

The system 70 includes an ETC device 74 suitably connected to a plurality of implantable leads 22. The ETC device 74 is similar to the ETC device 64 of FIG. 5, except that it does not include the pacing unit 68. The ETC device 74 operates similarly to the ETC device 64, except that it does not have the pacing capacity of the ETC device 64 and is therefore not capable of pacing of the heart.

It is noted that, while the devices 1, 21 and 24 of FIGS. 1, 3 and 4, respectively, and the systems 60 and 70 of FIGS. 5 and 6, respectively, may use the single threshold crossing detection method disclosed in detail hereinabove, all of these devices and systems may use other detection methods. The detection methods for detecting depolarization events in the electrical signals sensed by one or more of the electrodes included in one or more of the implantable leads such as the leads 2, 4, and 6 of the device 1 and the plurality of implantable leads 22 of the devices 21 and 24 and the systems 60 and 70, may include detection methods known in the art for detection of locally sensed cardiac depolarization events based on signal morphology and/or methods based on multiple threshold crossings and/or signal slope as disclosed hereinabove.

Thus, various detection methods may be used for detecting the first event occurring within the alert window time interval ΔT3 (FIG. 2) as disclosed hereinabove.

Figure 7:
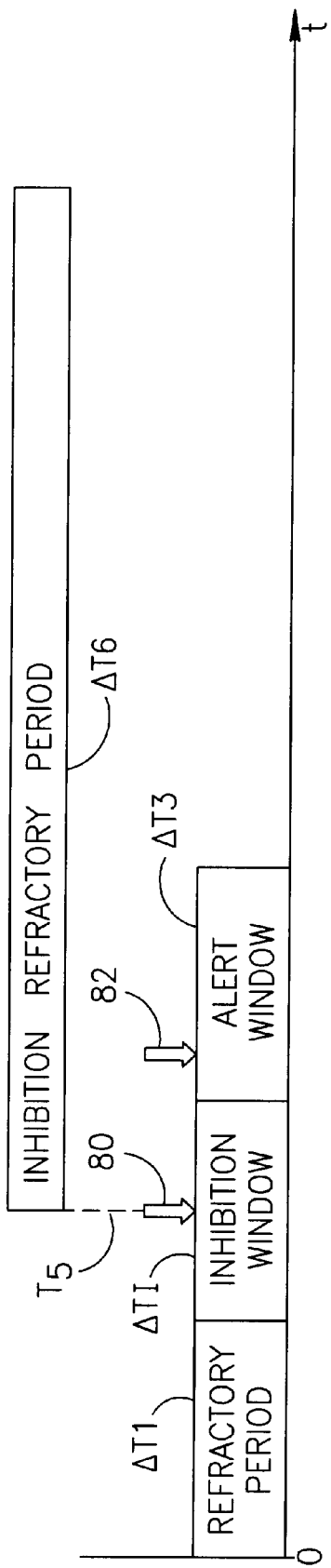
FIGS. 7 and 8 are schematic diagrams useful in understanding the method of timing of delivery of ETC signals of the present invention.
Figure 8:
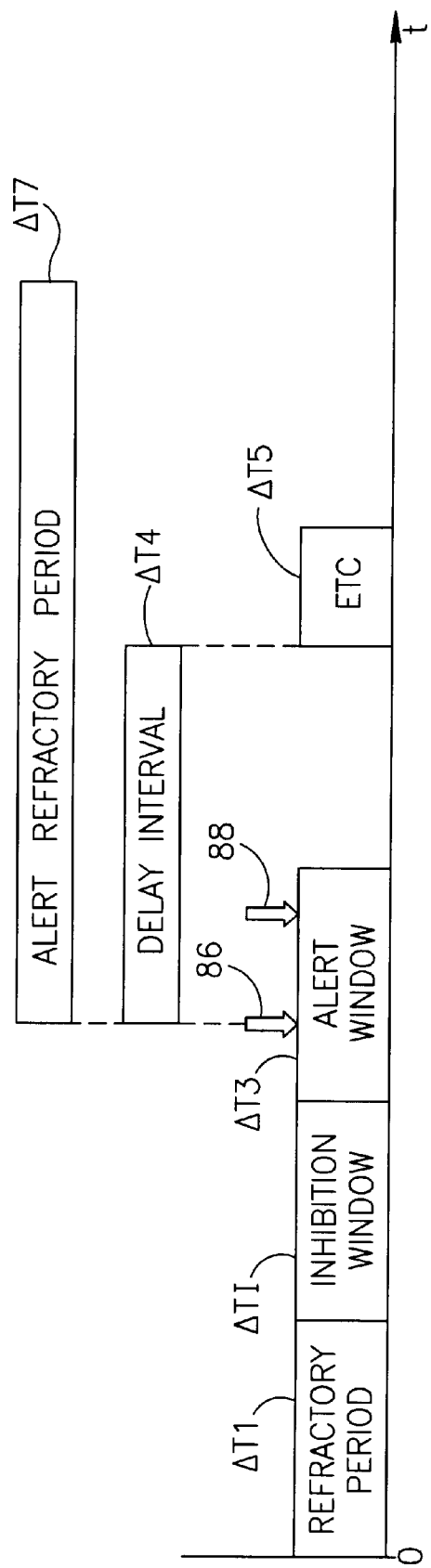

Reference is now made to FIGS. 7 and 8 which are schematic diagrams useful in understanding the method of timing of delivery of ETC signals of the present invention.

In each of FIGS. 7–8, The horizontal axis represents time and the zero time point of the horizontal axis represents the time of detection of a depolarization event locally sensed in the right ventricle 9 (FIG. 1) and is equivalent to the depolarization event 11 of FIG. 2. The refractory period ΔT1, the inhibition window ΔTI, the alert window ΔT3, the delay interval ΔT4, the ETC signal duration ΔT5, and the alert refractory period ΔT7 of FIGS. 7–8 are as disclosed in detail hereinabove, and illustrated in FIG. 2.

In FIG. 7, the arrow labeled 80 represents a depolarization event 80 locally sensed in the left ventricle 10 and detected at the time point represented by the dashed line labeled $T_5$. The arrow labeled 82 represents the time of occurrence of another depolarization 82 occurring in the left ventricle 10 at a time point which falls within the duration of the alert window $\Delta T3$. The time of detection of the depolarization event 80 falls within the duration of the inhibition window $\Delta TI$. Therefore, the delivery of an ETC pulse in response to the depolarization event 82 is inhibited. Preferably, the inhibition is implemented by triggering an "inhibition refractory period" $\Delta T6$ starting at the time of detection of the depolarization event 80 and having a duration $\Delta T6$. During the inhibition refractory period $\Delta T6$, local sensing in the left ventricle 10 is disabled so that no detection of threshold crossings is possible, effectively inhibiting the triggering of the delivery of an ETC signal within the duration of the inhibition refractory period $\Delta T6$.

Preferably, the duration of the inhibition refractory period $\Delta T6$ is calculated each time a local depolarization event is detected within the inhibition window $\Delta TI$ of the current beat cycle, by using the value of $T_5$ and the known values of $\Delta T2$, $\Delta T3$, $\Delta T4$ and $\Delta T5_{MAX}$. For example, the value of $T_5$ may be obtained by the software embedded within the device 1 of FIG. 1 (or embedded within other devices such as the devices 21, 24, 64 and 74 of FIGS. 3, 4, 5, and 6, respectively) by starting a timer (not shown) at time zero and recording the value of $T_5$ upon detection of a depolarization event, such as the depolarization event 80, within the duration of the inhibition window $\Delta TI$. The method of determining the time of a detected depolarization is well known in the art and will not be further discussed hereinafter.

Preferably, The inhibition refractory period $\Delta T6$ satisfies the inequality defined in equation 1.

$$\Delta T6 > (\Delta T2 - T_5) + \Delta T3 + \Delta T4 + \Delta T5_{MAX} \tag{1}$$

After detecting the depolarization event 80, the duration $\Delta T6$ is determined by calculating its value using equation 2.

$$\Delta T6 = (\Delta T2 - T_5) + \Delta T3 + \Delta T4 + \Delta T5_{MAX} + \Delta TX \tag{2}$$

wherein $\Delta TX$ is a predetermined constant time interval which ensures that the inequality of equation 1 is satisfied. Typically, the value of $\Delta TX$ may be in the range 1–100 milliseconds. However, other values of $\Delta TX$ may be used depending, inter alia, on the specific implementation of the method.

Typically, the duration of the inhibition refractory period $\Delta T6$ is in the range of approximately 150–200 milliseconds, depending, inter alia, on the value of $T_5$ and on the preset value of $\Delta TX$. However, other suitable values of the duration of the inhibition refractory period $\Delta T6$ may also be used. Preferably, the total duration of $\Delta T6$ should not be excessively long since using an excessively long duration of the inhibition refractory period $\Delta T6$ may result in undesirable extending of the period of disabling the sensing in the left ventricle 10 which may prevent the detection of relevant depolarization events such as, for example, depolarization events due to ectopic beats.

It is noted that, the method disclosed hereinabove for determining the value of $T_5$ is given by way of example only, and that other different methods for determining the time of detection of a depolarization event within the duration of the inhibition window $\Delta TI$ may be used.

It is noted that, in accordance with another preferred embodiment of the present invention, the value of the inhibition refractory period $\Delta T6$ may a preset value which is used irrespective of the actual value of $T_5$. In this preferred embodiment, the preset value of $\Delta T6$ used is preferably set such that it is equal to or larger than the sum of the inhibition window duration $\Delta TI$, the alert window duration $\Delta T3$, the delay interval $\Delta T4$ and the maximal allowable duration $\Delta T5_{MAX}$ of the ETC signal ($\Delta T6 \geq \Delta TI + \Delta T3 + \Delta T4 + \Delta T5_{MAX}$).

In FIG. 8, the arrow labeled 86 represents the time of detection of a depolarization event 86 locally sensed in the left ventricle 10. The depolarization event 86 is locally sensed in the left ventricle 10 at a time point which falls within the duration of the alert window $\Delta T3$. Since no depolarization is detected within the inhibition window $\Delta TI$, the depolarization event 86 which is the earliest depolarization event detected within the alert window $\Delta T3$ triggers the delivery of an ETC signal $\Delta T5$. The ETC signal $\Delta T5$ is delivered to the left ventricle 10 after a delay interval $\Delta T4$.

The detection of the earliest depolarization event 86 within the alert window $\Delta T3$ also triggers the initiation of the alert refractory period $\Delta T7$ as disclosed in detail hereinabove and illustrated in FIG. 2, disabling the local sensing of electrical events at the left ventricle 10 for the duration of the alert refractory period $\Delta T7$, and preventing any subsequent depolarization occurring within the duration of the alert refractory period $\Delta T7$ from triggering additional ETC signals within the current beat cycle. For example, the arrow labeled 88 represents the time of occurrence of a depolarization 88 in the left ventricle 10. The depolarization event 88 occurs at a time later than the detection time of the depolarization event 86 and falls within the duration of the alert refractory period $\Delta T7$. Since the sensing in the left ventricle 10 is disabled during the duration of the alert refractory period $\Delta T7$, the depolarization 88 would not be sensed and would therefore not be detected. The disabling of the local sensing of electrical signals in the left ventricle 10 after the initiation of the alert refractory period thus prevents the delivering of an additional ETC signal within the same beat cycle by a potentially threshold-crossing depolarization event due to an ectopic beat, electrical noise and the like and therefore reduces the probability of delivering improperly timed ETC signals which may be arrhythmogenic.

After the alert refractory period $\Delta T7$ terminates, the local sensing of depolarization signals in the left ventricle 10 is re-enabled.

It is noted that, many other suitable methods of event detection using IEGM single or multiple threshold crossing, IEGM signal slope criteria and signal morphology detection methods as disclosed hereinabove or various combinations thereof may be used in the ETC signal timing method of the present invention.

It will be appreciated by those skilled in the art that, while in the schematic diagrams of FIGS. 7 and 8 the time axis zero point on the horizontal axis represents the local detection of a depolarization event at or about the right ventricle 9, the events such as the events 80, and 86, represent depolarization events locally detected at or about the left ventricle 10, and the depolarizations 82 and 88 represent depolarizations occurring at or about the left ventricle 10, other preferred embodiments are possible in which the time axis zero point represents the local detection of a depolarization event at or about the right atrium 8, the detected events such as the events 80, and 86 represent depolarization events locally detected at or about the left ventricle 10, and the depolarizations 82 and 88 represent depolarizations occurring in or about the left ventricle 10. Such preferred embodiments may have various different electrode and lead configurations (not shown). For example, in one exemplary preferred embodiment, the device 1 may include the lead 2 and electrode(s) 2A for local sensing in or about the right atrium 8, and the lead 6 and electrode(s) 6A for local sensing in or about the left ventricle 10 and for delivering ETC signals to the left ventricle 10, while the lead 4 and the electrode(s) 4A are omitted. In such a case, pacing may be performed, if required, in the right atrium 8 by using the electrode(s) 2A and in the left ventricle 10 by using the electrode(s) 6A, but not in the right ventricle 9.

In another exemplary preferred embodiment of the invention, the device 1 may include the lead 4 and electrode(s) 4A for local sensing in or about the right ventricle 9, and the lead 6 and electrode(s) 6A for local sensing in or about the left ventricle 10 and for delivering ETC signals to the left ventricle 10, while the lead 2 and the electrode(s) 2A are omitted. In such an embodiment, pacing may be performed, if required, in the right ventricle by the electrode(s) 4A and in the left ventricle 10 by the electrode(s) 6A.

It is noted that, in the preferred embodiments in which the device 1 includes a pacing unit, the electrode(s) 6A may be used for delivering a pacing pulse (not shown) to the left ventricle 10 within a cardiac beat cycle and for delivering an ETC signal (not shown) to the left ventricle 10 within the same beat cycle. However, the electrode(s) 6A may also be used for sensing in beat cycles where no pacing or ETC signal is required, or for sensing and pacing in beat cycles where pacing is required but no ETC signal delivery is required.

Similarly, other preferred embodiments of the present inventions are possible in which the leads 2, 4 and 6 or the leads 22 include one or more electrodes (not shown) having different functions. For example, the lead 2 of the device 1 of FIG. 1 may include two separate electrodes (not shown) or two separate electrode pairs (not shown) one of these electrodes or electrode pairs is used for local sensing in or about the right atrium 8 and the other of these electrodes or electrode pairs is used for pacing the right atrium 8. This electrode arrangement may be implemented in cases where the same electrode(s) are not capable of being used for sensing and for ETC signal delivery within the same beat cycle due to electrode polarization problems. In another embodiment, the lead 4 of the device 1 of FIG. 1 may include two separate electrodes (not shown) or electrode pairs (not shown) one of these electrodes or electrode pairs is used for local sensing in or about the right ventricle 9 and the other of these electrodes or electrode pairs is used for pacing the right ventricle 9. In yet another preferred embodiment of the present invention, the lead 6 of the device 1 of FIG. 1 may include two separate electrodes (not shown) or electrode pairs one of these electrodes or electrode pairs is used for local sensing in or about the left ventricle 10 and the other of these electrodes is used for delivering ETC signals to the left ventricle 10.

Additionally, other preferred embodiments of the present invention are possible, which have different combinations of lead and/or electrode arrangements different than the combinations of lead and/or electrode arrangements disclosed hereinabove. For example, in accordance with one preferred embodiment of the present invention, the lead 2 includes a single sensing/pacing electrode 2A, the lead 4 includes a single sensing/pacing electrode 4A and the lead 6 includes one electrode (not shown) for sensing and another electrode (not shown) for delivering ETC signals. Many other permutations and combinations of electrodes and leads are therefor possible in other preferred embodiments of the present invention. For example, various electrode pairs or electrode arrays may be used in place of the single electrodes 2A, 4A and 6A of FIG. 1 or within the implantable leads 22 of FIGS. 3–6 for sensing and/or pacing and/or delivering of ETC signals to appropriate sites within the heart.

It is noted that the devices disclosed hereinabove may also be modified to include the appropriate electrical circuitry for delivering electrical defibrillating signals to the heart. For example the implantable devices 1, 21 and 24 disclosed hereinabove may also include integrated defibrilator units (not shown) and the programs embedded within the controller unit 40 may be adapted to control the delivery of cardioverting and/or defibrillating signals to the heart as is known in the art. For example, U.S. Pat. No. 4,830,006 to Haluska titled "IMPLANTABLE CARDIAC STIMULATOR FOR DETECTION AND TREATMENT OF ARRYTHMIAS" discloses a device for performing pacing-type therapies and cardioversion and defibrillation shock-type therapies. The implantable devices 1, 21, and 24 may be adapted for performing such pacing-type therapies and cardioversion and defibrillation shock-type therapies.

It is further noted that, in all the embodiments of the devices disclosed hereinabove and illustrated in the drawings, the electrical power sources of the devices are not shown for the sake of clarity of illustration. Such power sources, for example, batteries and/or line operated power supplies or the like, may be internal power sources included in the implantable devices 21, 24 or external power sources of the devices 64 and 74, and which are used to provide power to the electronic circuitry of these devices, are well known in the art and are not disclosed in detail hereinabove.

While the invention has been described with respect to a limited number of embodiments, it will be appreciated by those skilled in the art that many variations, modifications and other applications of the invention may be made.

What is claimed is:

1. Apparatus for timing the delivery of a non-excitatory cardiac contractility modulating signal to a heart within a cardiac beat cycle of said heart, the apparatus is operatively connectable to a plurality of electrodes adapted to be implanted in said heart, the apparatus comprising:

an excitable tissue control unit operatively connectable to at least one electrode of said plurality of electrodes for delivering said non-excitatory signal to said heart;

a detecting unit operatively connectable to a first electrode of said plurality of electrodes for sensing activity in a first cardiac site and for detecting a first electrical depolarization event within said cycle, said detecting unit is also operatively connectable to a second electrode of said plurality of electrodes for sensing electrical activity in a second cardiac site and for detecting at least a second electrical depolarization event within said beat cycle;

a controller unit operatively connected to said excitable tissue control unit and to said detecting unit, for controlling the operation of said excitable tissue control unit and said detecting unit, for receiving from said detecting unit signals representing the detection of said first electrical depolarization event and said second electrical depolarization event, and for controlling the applying, through at least one of said plurality of electrodes, of said non-excitatory signal to said second cardiac site or in the vicinity thereof in response to the detecting of said at least second electrical depolarization event by said detecting unit within an alert window period, said alert window period starts at a first delay from the time of detection of said first electrical depolarization event and has a first duration, said applying is delayed from the time of detecting of said at least second electrical depolarization event.

2. The apparatus according to claim 1 wherein said controller is adapted to inhibit said applying of said non-excitatory signal in response to receiving from said detecting unit a signal representing the detecting at said second site of a third electrical depolarization event preceding said second electrical depolarization event, said third electrical depolarization event is detected within an inhibition window period, said inhibition window period starts at a second delay from the time of detection of said first electrical depolarization event and terminated at or before the time of starting of said alert window period, said second delay is smaller than said first delay.

3. The apparatus according to claim 2 wherein said controller is adapted for initiating an inhibition refractory period, said inhibition refractory period is initiated by said signal representing the detecting at said second site of said third electrical depolarization event by said detecting unit, said inhibition refractory period has a second duration, said controller is adapted for disabling the sensing by said detecting unit of said electrical activity in said at least second site during said inhibition refractory period.

4. The apparatus according to claim 3 wherein said second duration of said inhibition refractory period is a present duration.

5. The apparatus according to claim 3 wherein said second duration of said inhibition refractory period is equal to or larger than the value obtained by summing said inhibition window period, said first duration, said second delay and the maximal allowable duration of said non-excitatory signal.

6. The apparatus according to claim 3 wherein the said controller is adapted to determine the value of said second duration for said inhibition refractory period from the time of detecting of said third electrical depolarization event within said beat cycle and from the present values of said first duration of said alert window, said first delay and the maximal allowable duration of said non-excitatory signal.

7. The apparatus according to claim 6 wherein said second duration is larger than the value obtained by subtracting said time of detecting of said third electrical depolarization event from the sum of said first delay, said first duration, said second delay and said maximal allowable duration of said non-excitatory signal.

8. The apparatus according to claim 1 wherein said detecting unit is adapted for detecting at least one of said first electrical depolarization event and said second electrical depolarization event by using an event detection method selected from a threshold crossing detection method, a detection method based on one or more morphological parameters of said electrical activity, a slope based detection method, and any combination thereof.

9. The apparatus according to claim 1 wherein said detecting unit is selected from an analog detecting unit and a signal detecting unit.

10. The apparatus according to claim 1 wherein said controller unit is selected from a central processing unit, a micro-controller unit, a digital signal processing unit, a computer, a workstation, and any combination thereof.

11. The apparatus according to claim 1 further including an implantable housing, wherein said detecting unit, said excitable tissue control unit and said controller unit are contained within said housing.

12. The apparatus according to claim 11 further including a telemetry unit disposed within said housing and operatively connected to said controller.

13. The apparatus according to claim 1 wherein said plurality of electrodes is implanted within said patient, and wherein said excitable tissue control unit, said detecting unit, and said controller unit are disposed outside of said patient.

14. The apparatus according to claim 1 wherein said first electrode is implanted in or about the right ventricle of said heart and said second electrode is implanted in or about the left ventricle of said heart.

15. The apparatus according to claim 1 wherein said first electrode is implanted in or about the right atrium of said heart and said second site is located in or about the left ventricle of said heart.

16. The apparatus according to claim 1 further including a pacing unit operatively connectable to at least one electrode of said plurality of electrodes, said pacing unit is configured for delivering pacing pulses to said heart, said controller unit is operatively connected to said pacing unit for controlling the operation thereof.

17. The apparatus according to claim 16 wherein said first electrode is implanted in or about the right ventricle of said heart and said second electrode is implanted in or about the left ventricle of said heart.

18. The apparatus according to claim 17 wherein said first electrode is operatively connectable to said pacing unit for pacing said right ventricle.

19. The apparatus according to claim 17 wherein said second electrode is operatively connectable to said pacing unit for pacing said left ventricle.

20. The apparatus according to claim 17 wherein at least one electrode of said plurality of electrodes is operatively connectable to said pacing unit and is implanted in or about the right atrium for pacing said right atrium.

21. The apparatus according to claim 17 wherein said first electrode is implanted in or about the right atrium of said heart and said second electrode is implanted in or about the left ventricle of said heart.

22. The apparatus according to claim 21 wherein said first electrode is operatively connectable to said pacing unit for pacing said right atrium.

23. The apparatus according to claim 21 wherein said second electrode is operatively connectable to said pacing unit for pacing said left ventricle.

24. The apparatus according to claim 21 wherein at least one of said electrodes is implanted in or about the right ventricle of said heart and is operatively connectable to said pacing unit for pacing said right ventricle.

25. The apparatus according to claim 1 wherein said controller is configured for controlling said excitable tissue control unit to deliver said non-excitatory signal in response to the detection of the earliest electrical depolarization event of said at least second electrical depolarization event within said alert window period.

26. The apparatus according to claim 25 wherein said controller is configured for initiating an alert refractory period in response to the detection of said earliest electrical depolarization event, said alert refractory period starts at the time of detection of said earliest electrical depolarization event and has a third duration, said alert refractory period ends within the duration of said beat cycle, wherein during said alert refractory period said sensing and said detecting of said detecting unit is disabled.

27. The apparatus according to claim 26 wherein said third duration of said alert refractory period is a preset value.

28. The apparatus according to claim 26 wherein said third duration of said alert refractory period is larger than the sum of said first duration, said second delay and the maximum allowable duration of said non-excitatory signal.

29. Apparatus for timing the delivery of a non-excitatory cardiac contractility modulating signal to a heart within a cardiac beat cycle of said heart, the apparatus is operatively connectable to a plurality of electrodes adapted to be implanted in said heart, the apparatus comprising:

means for delivering non-excitatory cardiac contractility modulating signals to said heart;

event detecting means operatively connectable to a first electrode of said plurality of electrodes for sensing electrical activity at or about a first cardiac site and for detecting a first event within said beat cycle, said first event is associated with cardiac activation at or about said first cardiac site, said event detecting means is also operatively connectable to a second electrode of said plurality of electrode for sensing electrical activity at or about a second cardiac site and for detecting at least a second event at or about said first cardiac site within said beat cycle, said at least second event is associated with cardiac activation at or about said second cardiac site;

controller means operatively connected to said means for delivering non-excitatory cardiac contractility modulating signals and to said event detecting means, for controlling the operation of said means for delivering non-excitatory cardiac contractility modulating signals, for receiving from said event detecting means signals representing the detection of said first event and said second event and for controlling the applying by said means for delivering, of said non-excitatory cardiac contractility modulating signal to said second cardiac site, in response to the detecting of said at least second event by said event detecting means within an alert window period, said alert window period starts at a first delay from the time of detection of said first event and has a first duration, said applying is delayed from the time of detecting of said at least second event.

30. Apparatus for timing the delivery of a non-excitatory cardiac contractility modulating signal to a heart within a cardiac beat cycle of said heart, the apparatus is operatively connectable to a plurality of electrodes adapted to be implanted in said heart, the apparatus comprising:

an excitable tissue control unit operatively connectable to at least one electrode of said plurality of electrodes and configured for delivering said non-excitatory signal to said heart;

at least one detecting unit operatively connectable to a first electrode of said plurality of electrodes for sensing electrical activity in a first cardiac site and for detecting a first electrical depolarization event within said beat cycle, said at least one detecting unit is operatively connectable to a second electrode of said plurality of electrodes for sensing electrical activity in a second cardiac site and for detecting at least a second electrical depolarization event within said beat cycle; and a controller unit operatively connected to said excitable tissue control unit and to said at least one detecting unit, for controlling the operation of said excitable tissue control unit and said detecting unit, for receiving from said detecting unit signals representing the detection of said first electrical depolarization event and said second electrical depolarization event and for controlling the applying, through at least one of said plurality of electrodes, of said non-excitatory signal to said second cardiac site or in the vicinity thereof in response to the detecting of said at least second electrical depolarization event by said detecting unit within an alert window period, said alert window period starts at a first delay from the time of detection of said first electrical depolarization event and has a first duration, said applying is delayed from the time of detecting of said at least second electrical depolarization event.

31. Apparatus for timing the delivery of a non-excitatory cardiac contractility modulating signal to a heart within a cardiac beat cycle of said heart, the apparatus is operatively connectable to a plurality of electrodes adapted to be implanted in said heart, the apparatus comprising:

an excitable tissue control unit operatively connectable to at least one electrode of said plurality of electrodes for delivering said non-excitatory signal to said heart;

a detecting unit operatively connectable to a first electrode of said plurality of electrodes for sensing electrical activity in a first cardiac site and for detecting a first electrical depolarization event within said beat cycle, said detecting unit is also operatively connectable to a second electrode of said plurality of electrodes for sensing electrical activity in a second cardiac site and for detecting at least a second electrical depolarization event within said beat cycle;

a controller unit operatively connected to said excitable tissue control unit and to said detecting unit, for controlling the operation of said excitable tissue control unit and said detecting unit, for receiving from said detecting unit signals representing the detection of said first electrical depolarization event and said second electrical depolarization event, and for controlling the applying, through at least one of said plurality of electrodes, of said non-excitatory signal to said second cardiac site or in the vicinity thereof in response to the detection of said at least second electrical depolarization event by said detecting unit within an alert window period, said alert window period starts at a first delay from the time of detection of said first electrical depolarization event and has a first duration, said applying is delayed from the time of detecting of said at least second electrical depolarization event; and a power source for providing power to said excitable tissue control unit, said detecting unit and said controller unit.

32. The apparatus according to claim 31 further including a pacing unit operatively connectable to at least one electrode of said plurality of electrodes, said pacing unit is configured for delivering pacing pulses to said heart, said controller unit is operatively connected to said pacing unit for controlling the operation thereof.

* * * * *